US007553655B2

(12) United States Patent
Mehta et al.

(10) Patent No.: US 7,553,655 B2
(45) Date of Patent: Jun. 30, 2009

(54) BACTERIAL HOST CELL FOR THE DIRECT EXPRESSION OF PEPTIDES

(75) Inventors: Nozer M. Mehta, Randolph, NJ (US); Angelo P. Consalvo, Monroe, NY (US); Martha V. L. Ray, Nutley, NJ (US); Christopher P. Meenan, Lincoln Park, NJ (US)

(73) Assignee: Unigene Laboratories Inc., Boonton, NJ (US)

( * ) Notice: Subject to any disclaimer, the term of this patent is extended or adjusted under 35 U.S.C. 154(b) by 0 days.

(21) Appl. No.: 11/929,079

(22) Filed: Oct. 30, 2007

(65) Prior Publication Data

US 2008/0102510 A1    May 1, 2008

Related U.S. Application Data

(62) Division of application No. 11/076,260, filed on Mar. 9, 2005.

(60) Provisional application No. 60/552,824, filed on Mar. 12, 2004.

(51) Int. Cl.
*C12N 1/20* (2006.01)
*C12N 15/00* (2006.01)

(52) U.S. Cl. .............. 435/252.33; 435/252.1; 435/320.1

(58) Field of Classification Search ............ 435/252.33, 435/252.1, 320.1
See application file for complete search history.

(56) References Cited

U.S. PATENT DOCUMENTS

| 4,595,658 | A | 6/1986 | Zinder et al. ............ 435/69.1 |
| 5,223,407 | A | 6/1993 | Wong et al. ............ 435/69.1 |
| 6,103,495 | A * | 8/2000 | Mehta et al. ............ 435/69.1 |
| 6,210,925 | B1 | 4/2001 | Mehta et al. ............ 435/69.1 |
| 6,627,438 | B2 * | 9/2003 | Mehta et al. ............ 435/320.1 |
| 6,737,250 | B2 | 5/2004 | Mehta et al. ............ 435/69.1 |
| 2005/0221442 | A1 | 10/2005 | Mehta et al. |

FOREIGN PATENT DOCUMENTS

| EP | 0 177 343 | 2/1985 |
| WO | WO 98/46722 | 10/1998 |

OTHER PUBLICATIONS

Promega 1997 catalog, p. 15, PinPointTM Xa1 T-vector.*
Ray et al., Production of salmon calcitonin by direct expression of a glycine-extended precursor in *Escherichia coli*. Prote Purif. 26(2): 249-59, 2002.*
New England Biolabs 1995 Catalog (pp. 146, and 148-155).*
Ray, et al., "Production of Recombinant Salmon Calcitonin by In Vitro Amidation of an *Escherichia coli* Produced Precursor Peptide." *Bio/Technology*, 11:64-70 (1993).

Watson, "Compilation of Published Signal Sequences." *Nucleic Acids Research*, 12(13):5145-5164 (1984).
Hsiung, et al., "High-Level Expression, Efficient Secretion and Folding of Human Growth Hormone in *Escherichia coli*." *Biotechnology*, 4:991-995 (1986).
Vaara, "Agents That Increase the Permeability of the Outer Membrane." *Microbiological Reviews*, 56:395-411 (1992).
Kaderbhai, et al., "Glycine-Induced Extracellular Secretion of a Recombinant Cytochrome Expressed in *Escherichia coli*." *Biotech. Appl. Biochem*, 25:53-61 (1997).
Nagaharu, et al., "Secretion Into the Culture Medium of a Foreign Gene Product From *Escherichia coli*: Use of the ompF Gene for Secretion of Human β-Endorphin." *Embo J.*, 4(13A):3589-3592 (1987).
Dykstra, et al., "Physical Characterization of the Cloned Protease III Gene From *Escherichia coli* K-12." *J. Bacteriol.*, 163:1055-1059 (1985).
Diaz-Torres, et al., "Extracellular Release of Protease III (ptr) by *Escherichia coli* K12." *Can. J. Microbiol.*, 37:718-721 (1991).
U.S. Appl. No. 10/818,966, filed Apr. 5, 2004 and claiming priority of Apr. 16, 1997 in the name of Nozer M. Mehta et al., entitled "Direct Expression of Peptides Into Culture Media", published as US 2004-0191865.
U.S. Appl. No. 11/928,936, filed Oct. 30, 2007, Mehta et al.
U.S. Appl. No. 11/928,994, filed Oct. 30, 2007, Mehta et al.
U.S. Appl. No. 11/929,028, filed Oct. 30, 2007, Mehta et al.
M. Ray et al., "Production of salmon calcitonin by direct expression of a glycine-extended precursor in *Escherichia coli*", *Protein Expression & Purification*, 26:249-259 (2002).
J. Winter et al., "Increased production of human proinsulin in the periplasmic space of *Escherichia coli* by fusion to DsbA", *Journal of Biotechnology*, 84:175-185 (2000).
New England Biolab. Catalog, 1995, 146, 148-155.
International Search Report dated Sep. 21, 2007.
Supplementary European Search Report dated Aug. 22, 2008 corresponding to European Patent Application No. 05734021.8.
"Construction and Characterization of *Escherichia coli* Strains Deficient in Multiple Secreted Proteases: Protease III Degrades High-Molecular-Weight Substrates In Vivo", Francois Baneyx and George Georgiou, Journal of Bacteriology, Apr. 1991, pp. 2696-2703, vol. 173, No. 8.
European Search Report dated Apr. 27, 2009 issued in corresponding European Application No. 09156191.0.

* cited by examiner

*Primary Examiner*—Thaian N. Ton
*Assistant Examiner*—Wu-Cheng Winston Shen
(74) *Attorney, Agent, or Firm*—Ostrolenk Faber LLP

(57) ABSTRACT

Expression systems are disclosed for the direct expression of peptide products into the culture media where genetically engineered host cells are grown. High yield was achieved with a special selection of hosts, and/or fermentation processes which include careful control of cell growth rate, and use of an inducer during growth phase. Special universal cloning vectors are provided for the preparation of expression vectors which include control regions having multiple promoters linked operably with coding regions encoding a signal peptide upstream from a coding region encoding the peptide of interest. Multiple transcription cassettes are also used to increase yield. The production of amidated peptides using the expression systems is also disclosed.

1 Claim, 9 Drawing Sheets

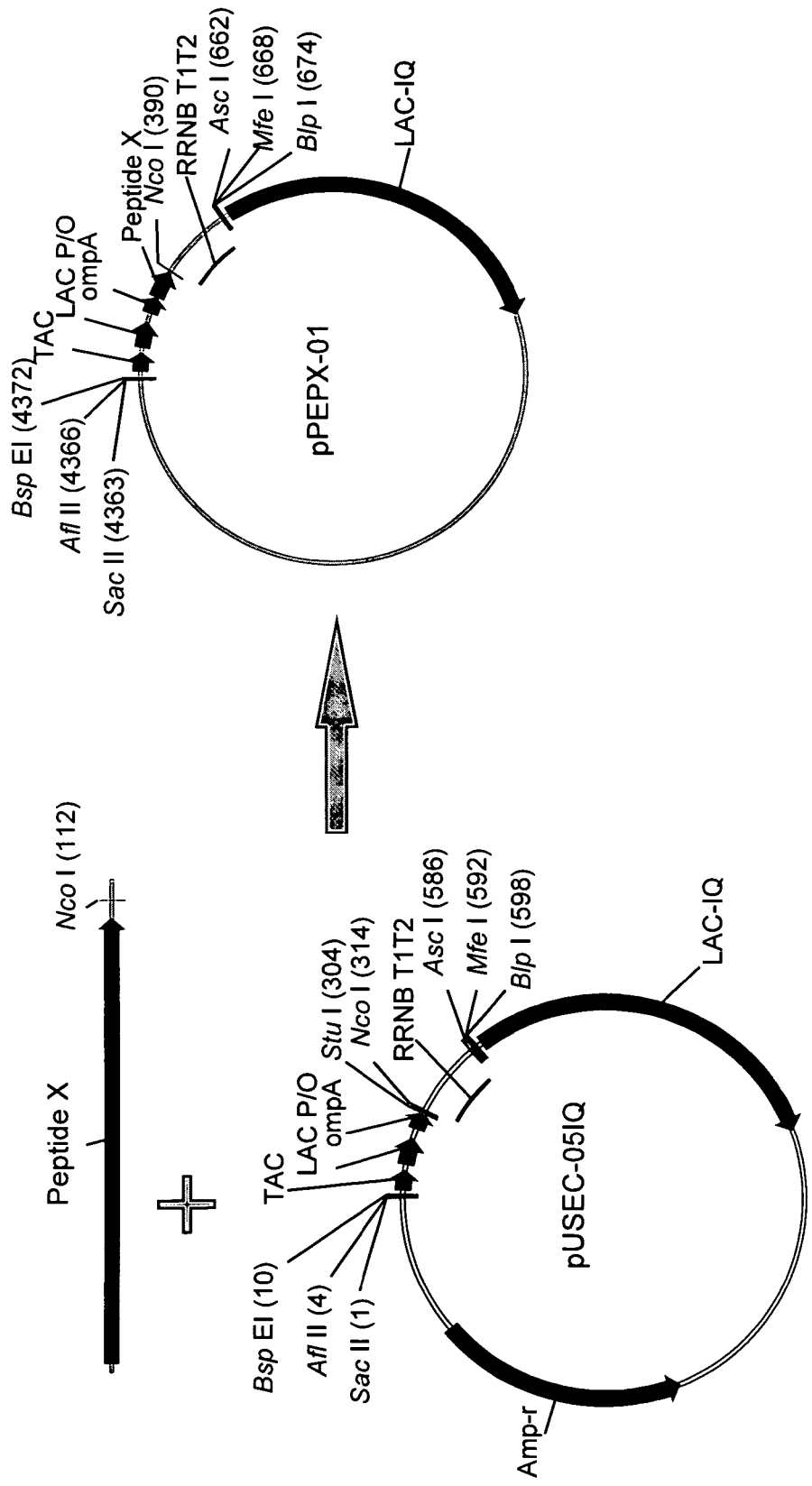
Cloning of Peptide X Step 1: Ligation of Peptide X into the secretion expression vector pUSEC-05IQ (Fig. 3A)

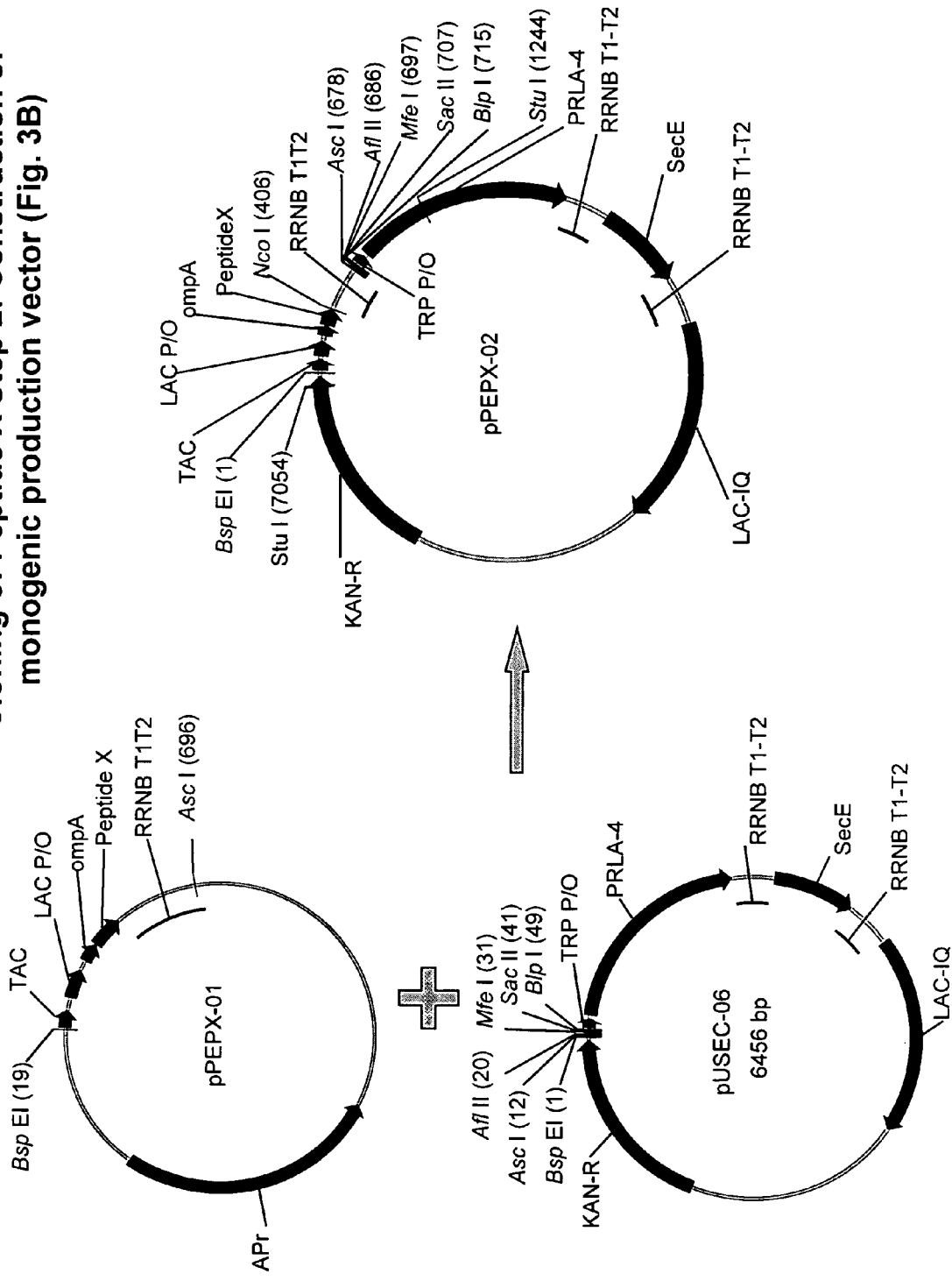

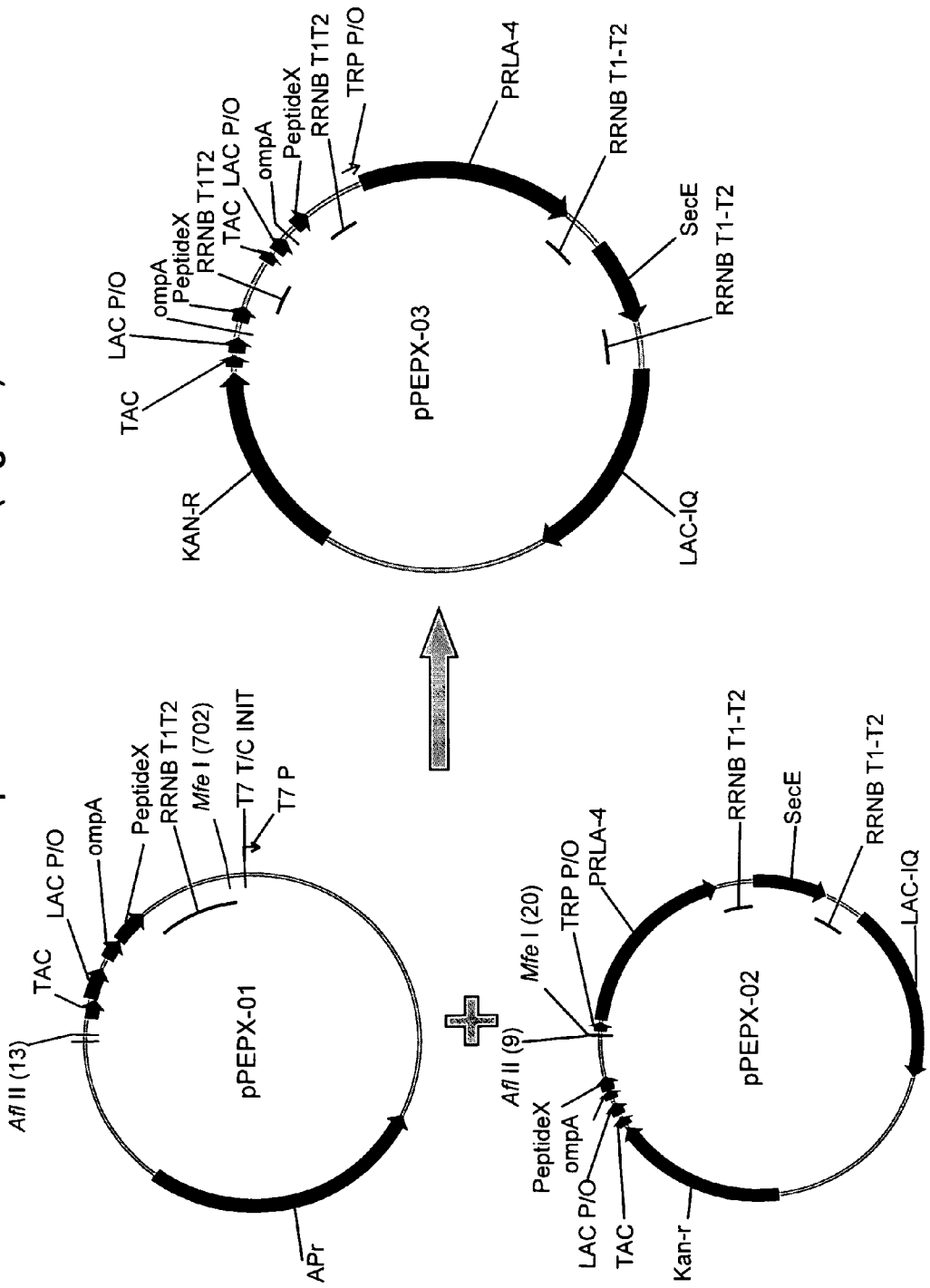

BACTERIAL HOST CELL FOR THE DIRECT EXPRESSION OF PEPTIDES

CROSS REFERENCE TO RELATED APPLICATIONS

The present application is a divisional of U.S. patent application Ser. No. 11/076,260, filed Mar. 9, 2005, which is a 35 U.S.C. §119 conversion of U.S. Provisional Application No. 60/552,824, filed Mar. 12, 2004, the contents of which are specifically incorporated herein.

FIELD OF THE INVENTION

The present invention relates to direct expression of a peptide product into the culture medium of genetically engineered host cells expressing the peptide product. More particularly, the invention relates to cloning vectors, expression vectors, host cells and/or fermentation methods for producing a peptide product that is excreted outside the host into the culture medium in high yield. In some embodiments, the invention relates to direct expression of a peptide product having C-terminal glycine which is thereafter converted to an amidated peptide having an amino group in place of said glycine.

DESCRIPTION OF THE RELATED ART

Various techniques exist for recombinant production of peptide products, i.e. any compound whose molecular structure includes a plurality of amino acids linked by a peptide bond. A problem when the foreign peptide product is small is that it is often readily degradable by endogenous proteases in the cytoplasm or periplasm of the host cell that was used to express the peptide. Other problems include achieving sufficient yield, and recovering the peptide in relatively pure form without altering its tertiary structure (which can undesirably diminish its ability to perform its basic function). To overcome the problem of small size, the prior art has frequently expressed the peptide product of interest as a fusion protein with another (usually larger) peptide and accumulated this fusion protein in the cytoplasm. The other peptide may serve several functions, for example to protect the peptide of interest from exposure to proteases present in the cytoplasm of the host. One such expression system is described in Ray et al., *Bio/Technology*, Vol. 11, pages 64-70, (1993).

However, the isolation of the peptide product using such technology requires cleavage of the fusion protein and purification from all the peptides normally present in the cytoplasm of the host. This may necessitate a number of other steps that can diminish the overall efficiency of the process. For example, where a prior art fusion protein is accumulated in the cytoplasm, the cells must usually be harvested and lysed, and the cell debris removed in a clarification step. All of this is avoided in accordance with the present invention wherein the peptide product of interest is expressed directly into, and recovered from, the culture media.

In the prior art it is often necessary to use an affinity chromatography step to purify the fusion protein, which must still undergo cleavage to separate the peptide of interest from its fusion partner. For example, in the above-identified *Bio/Technology* article, salmon calcitonin precursor was cleaved from its fusion partner using cyanogen bromide. That cleavage step necessitated still additional steps to protect cysteine sulfhydryl groups at positions 1 and 7 of the salmon calcitonin precursor. Sulfonation was used to provide protecting groups for the cysteines. That in turn altered the tertiary structure of salmon calcitonin precursor requiring subsequent renaturation of the precursor (and of course removal of the protecting groups).

The peptide product of the invention is expressed only with a signal sequence and is not expressed with a large fusion partner. The present invention results in "direct expression". It is expressed initially with a signal region joined to its N-terminal side. However, that signal region is post-translationally cleaved during the secretion of the peptide product into the periplasm of the cell. Thereafter, the peptide product diffuses or is otherwise excreted from the periplasm to the culture medium outside the cell, where it may be recovered in proper tertiary form. It is not linked to any fusion partner whose removal might first require cell lysing denaturation or modification, although in some embodiments of the invention, sulfonation is used to protect cysteine sulfhydryl groups during purification of the peptide product.

Another problem with the prior art's accumulation of the peptide product inside the cell, is that the accumulating product can be toxic to the cell and may therefore limit the amount of fusion protein that can be synthesized. Another problem with this approach is that the larger fusion partner usually constitutes the majority of the yield. For example, 90% of the production yield may be the larger fusion partner, thus resulting in only 10% of the yield pertaining to the peptide of interest. Yet another problem with this approach is that the fusion protein may form insoluble inclusion bodies within the cell, and solubilization of the inclusion bodies followed by cleavage may not yield biologically active peptides.

The prior art attempted to express the peptide together with a signal peptide attached to the N-terminus to direct the desired peptide product to be secreted into the periplasm (see EP 177,343, Genentech Inc.). Several signal peptides have been identified (see Watson, M. Nucleic Acids Research, Vol 12, No. 13, pp: 5145-5164). For example, Hsiung et al. (Biotechnology, Vol 4, November 1986, pp: 991-995) used the signal peptide of outer membrane protein A (OmpA) of *E. coli* to direct certain peptides into the periplasm. Most often, peptides secreted to the periplasm frequently tend to stay there with minimal excretion to the medium. An undesirable further step to disrupt or permealize the outer membrane may be required to release sufficient amounts of the periplasmic components. Some prior art attempts to excrete peptides from the periplasm to the culture media outside the cell have included compromising the integrity of the outer membrane barrier by having the host simultaneously express the desired peptide product containing a signal peptide along with a lytic peptide protein that causes the outer membrane to become permeable or leaky (U.S. Pat. No. 4,595,658). However, one needs to be careful in the amount of lytic peptide protein production so as to not compromise cellular integrity and kill the cells. Purification of the peptide of interest may also be made more difficult by this technique.

Aside from outer membrane destabilization techniques described above there are less stringent means of permeabilizing the outer membrane of gram negative bacteria. These methods do not necessarily cause destruction of the outer membrane that can lead to lower cell viability. These methods include but are not limited to the use of cationic agents (Martti Vaara, Microbiological Reviews, Vol. 56, pages 395-411 (1992)) and glycine (Kaderbhai et al., Biotech. Appl. Biochem, Vol. 25, pages 53-61 (1997)) Cationic agents permeabilize the outer membrane by interacting with and causing damage to the lipopolysaccharide backbone of the outer membrane. The amount of damage and disruption can be non lethal or lethal depending on the concentration used. Glycine can replace alanine residues in the peptide component of peptidoglycan. Peptidoglycan is one of the structural components of the outer cell wall of gram negative bacteria. Growing *E. coli* in high concentration of glycine increases the frequency of glycine-alanine replacement resulting in a defective cell wall, thus increasing permeability.

Another prior art method of causing excretion of a desired peptide product involves fusing the product to a carrier protein that is normally excreted into the medium (hemolysin) or an entire protein expressed on the outer membrane (e.g. ompF protein). For example, human β-endorphin can be excreted as a fusion protein by *E. coli* cells when bound to a fragment of the ompF protein (EMBO J., Vol 4, No. 13A, pp: 3589-3592, 1987). Isolation of the desired peptide product is difficult however, because it has to be separated from the carrier peptide, and involves some (though not all) of the drawbacks associated with expression of fusion peptides in the cytoplasm.

Yet another prior art approach genetically alters a host cell to create new strains that have a permeable outer membrane that is relatively incapable of retaining any periplasmic peptides or proteins. However, these new strains can be difficult to maintain and may require stringent conditions which adversely affect the yield of the desired peptide product.

Raymond Wong et al. (U.S. Pat. No. 5,223,407) devised yet another approach for excretion of peptide products by making a recombinant DNA construct comprising DNA coding for the heterologous protein coupled in reading frame with DNA coding for an ompA signal peptide and control region comprising a tac promoter. This system reports yields significantly less than those achievable using the present invention.

Although the prior art may permit proteins to be exported from the periplasm to the media, this can result in unhealthy cells which cannot easily be grown to the desirable high densities, thus adversely affecting product yield.

More recently, Mehta et al. (U.S. Pat. No. 6,210,925) disclosed expression systems for the direct expression of peptide products into the culture media where genetically engineered host cells are grown. High yield was achieved with novel vectors, a special selection of hosts, and/or fermentation processes which include careful control of cell growth rate, and use of an inducer during growth phase. Special vectors are provided which include control regions having multiple promoters linked operably with coding regions encoding a signal peptide upstream from a coding region encoding the peptide of interest. Multiple transcription cassettes are also used to increase yield.

The present invention seeks to produce peptide in yet higher yields with an efficient expression vector using novel genetically engineered host cells. The present invention also seeks to produce efficient expression vectors using novel universal cloning vectors.

SUMMARY OF THE INVENTION

Accordingly, it is an object of the present invention to have a peptide product accumulate in good yield in the medium in which peptide-producing host cells are growing. This is advantageous because the medium is relatively free of many cellular peptide contaminants.

It is another object of the invention to provide genetically engineered host cells that are particularly useful in expressing the novel expression vectors of the invention and having a peptide product accumulate in good yield in the medium in which peptide-producing host cells are growing.

It is another object of the invention to provide an improved fermentation process for increasing the yield of a peptide product expressed by genetically engineered host cells.

It is a further object of the invention to provide improved methods for the production of amidated peptides utilizing precursor peptides having C-terminal glycines, which precursors are amidated following direct expression into the culture medium in accordance with the invention.

Accordingly, the present invention provides a genetically engineered *E. coli* bacterium deficient in chromosomal genes rec A and ptr encoding recombination protein A and Protease III, respectively.

The present invention also provides a cloning vector comprising: (a) a control region comprising at least two promoters; (b) nucleic acids coding for a signal sequence; (c) two gene cloning enzyme restriction sites that allow for the cloning of a gene encoding a peptide in reading frame with said signal sequence and linked operably with said control region; (d) at least two cassette cloning enzyme restriction sites 3' from said gene cloning enzyme restriction sites; and (e) at least two cassette cloning enzyme restriction sites 5' from said control region, wherein all said restriction enzyme sites are different from each other and unique within said vector.

The present invention further provides a method of preparing an expression vector containing a plurality of transcription cassettes, each cassette comprising: (1) a coding region with nucleic acids coding for a peptide product coupled in reading frame 3' of nucleic acids coding for a signal peptide; and (2) a control region linked operably with the coding region, said control region comprising a plurality of promoters, said method comprising: (a) cloning into the cloning vector of the cloning vector of the present invention said coding region with nucleic acids coding for a peptide product in reading frame 3' of nucleic acids coding for the signal peptide using the two gene cloning enzyme restriction sites thereby forming an expression cassette within the cloning vector; (b) cutting the expression cassette from the cloning vector using a first restriction enzyme that cuts at a cassette cloning enzyme restriction site 3' from said gene cloning enzyme restriction sites and a second restriction enzyme that cuts at a cassette cloning enzyme restriction site 5' from said gene cloning enzyme restriction sites; (c) ligating the expression cassette into a template expression vector containing the cassette cloning enzyme restriction sites of step (b) such that the first restriction enzyme site is 3' from the second restriction enzyme sites wherein said template expression vector: (i) has been ligated with the first and second restriction enzymes, and (ii) contains at least one more pair of cassette cloning enzyme restriction sites, such as that first member of the pair is identical to a cassette cloning enzyme restriction site 3' from said gene cloning enzyme restriction sites of a cloning vector comprising: (1) a control region comprising a least two promoters; (2) nucleic acids coding for a signal sequence; (3) two gene cloning enzyme restriction sites that allow for the cloning of a gene encoding a peptide in reading frame with said signal sequence and linked operably with said control region; (4) at least two cassette cloning enzyme restriction sites 3' from said gene cloning enzyme restriction sites; and (5) at least two cassette cloning enzyme restriction sites 5' from said control region, wherein all said restriction enzyme sites are different from each other and unique within said vector, and the second member of the pair is identical to a cassette cloning enzyme restriction site 5' from said gene cloning enzyme restriction sites of a cloning vector comprising: (1) a control region comprising a least two promoters; (2) nucleic acids coding for a signal sequence; (3) two gene cloning enzyme restriction sites that allow for the cloning of a gene encoding a peptide in reading frame with said signal sequence and linked operably with said control region; (4) at least two cassette cloning enzyme restriction sites 3' from said gene cloning enzyme restriction sites; and (5) at least two cassette cloning enzyme restriction sites 5' from said control region, wherein all said restriction enzyme sites are different from each other and unique within said vector, wherein the first member of the pair is 3' from the second member of the pair and that each cassette cloning enzyme restriction site is unique to the template vector and no other cassette cloning enzyme restriction site of a cloning vector comprising: (1) a control region comprising a least two promoters; (2) nucleic acids coding for a signal sequence; (3) two gene cloning enzyme restriction sites that allow for the cloning of a gene encoding a peptide in reading frame with said signal sequence and linked operably with said control region; (4) at least two cassette cloning enzyme restriction sites 3' from said gene cloning enzyme restriction sites; and (5) at least two cassette cloning enzyme restriction sites 5' from said control region, wherein all said restriction enzyme sites are different from each other and unique within said vector, falls in an area 5' of the first and 3' of the second cassette cloning enzyme restriction sites, or in an area 5' of the first member of the pair and 3' of the second member of the pair of cassette cloning enzyme restriction sites; and (d) repeating steps (b) and (c) at least once but using restriction enzymes that cut the first member and the second member of any one of the pair of cassette cloning enzyme restriction sites instead of the first and second restriction enzymes of step (b).

The present invention also provides an E. coli host cell deficient in chromosomal genes rec A and ptr encoding recombination protein A and Protease III, respectively, said host containing and expressing an expression vector which comprises a plurality of transcription cassettes in tandem, each cassette comprising: (1) a coding region with nucleic acids coding for a peptide product coupled in reading frame 3' of nucleic acids coding for a signal peptide; and (2) a control region linked operably with the coding region, said control region comprising a plurality of promoters.

The present invention further provides a method of producing a peptide product which comprises culturing the host cell of the present invention transformed or transfected with the expression vector of the present invention in a culture medium and then recovering the peptide product from the medium in which the host cell has been cultured.

The present invention also provides a method of producing an amidated peptide product comprising the steps of: (a) culturing the host cell of the present invention transformed or transfected with the expression vector of the present invention in a culture medium wherein the peptide product includes a C-terminal glycine; (b) recovering said peptide product from said culture medium; and (c) converting said peptide product to an amidated peptide by converting said C-terminal glycine to an amino group.

BRIEF DESCRIPTION OF THE DRAWINGS

FIGS. 3A, 3B and 3C show a schematic diagram of the ligation of a generic peptide termed peptide X into the secretion expression vector pUSEC-05IQ (3A) to generate vector pPEPX-01 which is used along with vector pUSEC-06 to construct a monogenic production vector pPEPX-02 (3B) which is used to construct a digenic production vector pPEPX-03 (3C). In like manner, the construction of a trigenic vector would be accomplished by cutting the expression cassette from pPEPX-01 with SacII and BlPI and then ligating the cassette into pPEPX-03 digested with the same sites. The trigenic vector would, thus, be pPEPX-04.

DETAILED DESCRIPTION OF THE INVENTION

Figure 1A:
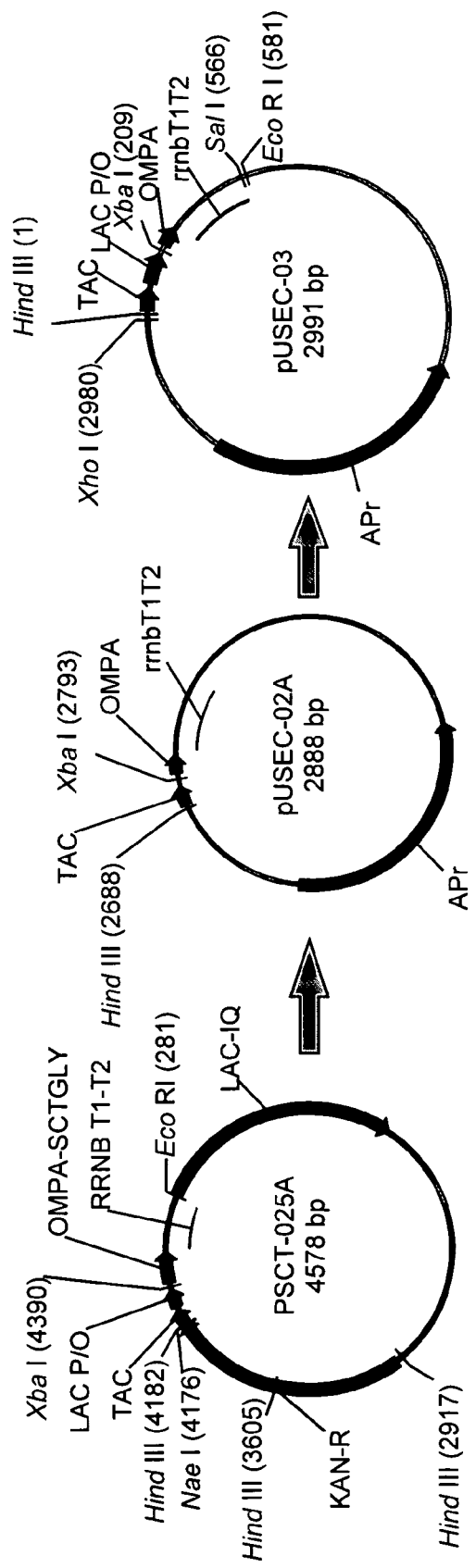
FIGS. 1A, 1B and 1C show a schematic diagram of the construction of the pUSEC-03 vector (1A) which is used in the construction of the pUSEC-05 vector (1B) which is in turn used in the construction of vector pUSEC-05IQ (1C) (ATCC Accession Number PTA-5567).
Figure 1B:
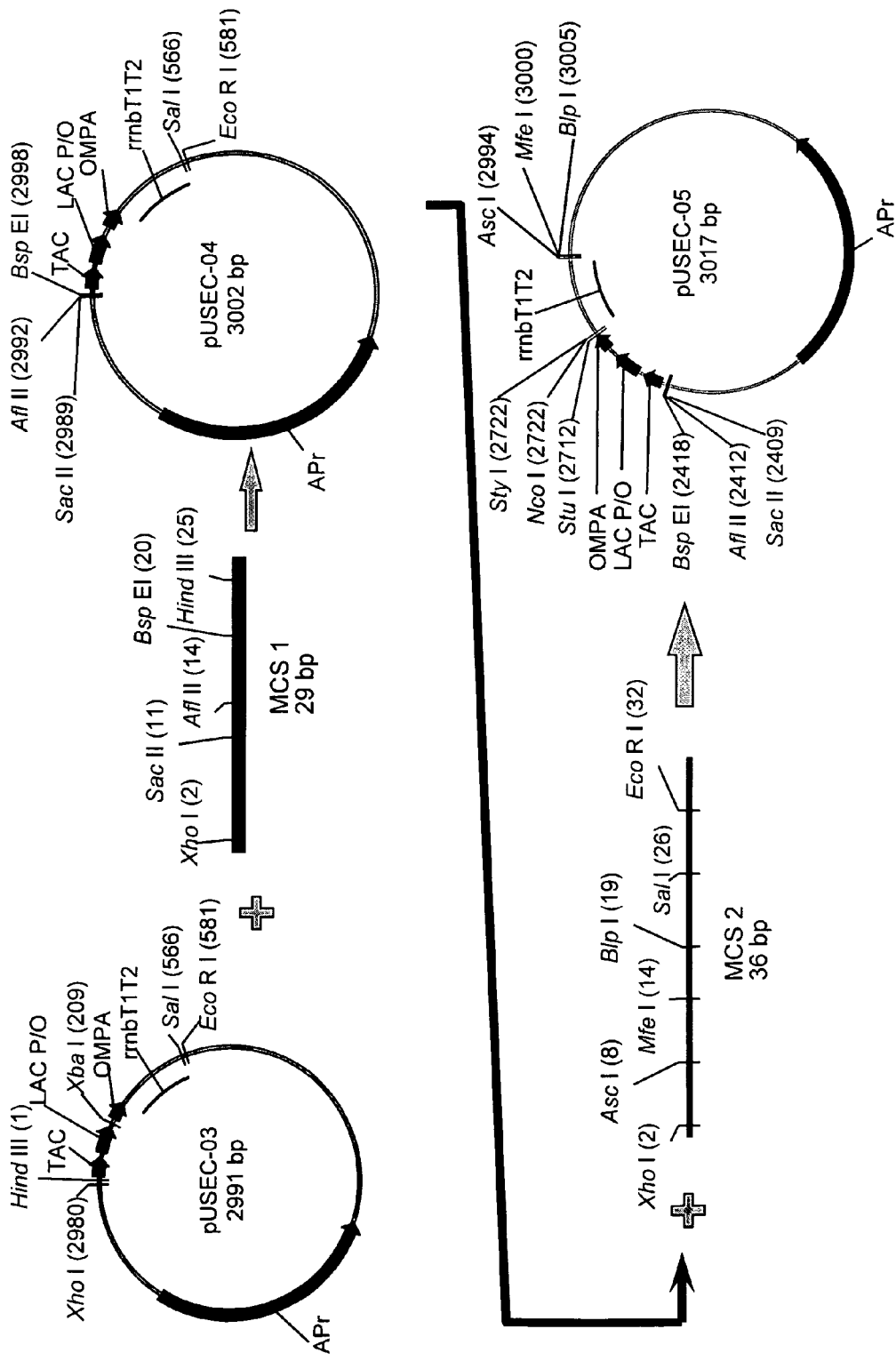
Figure 1C:
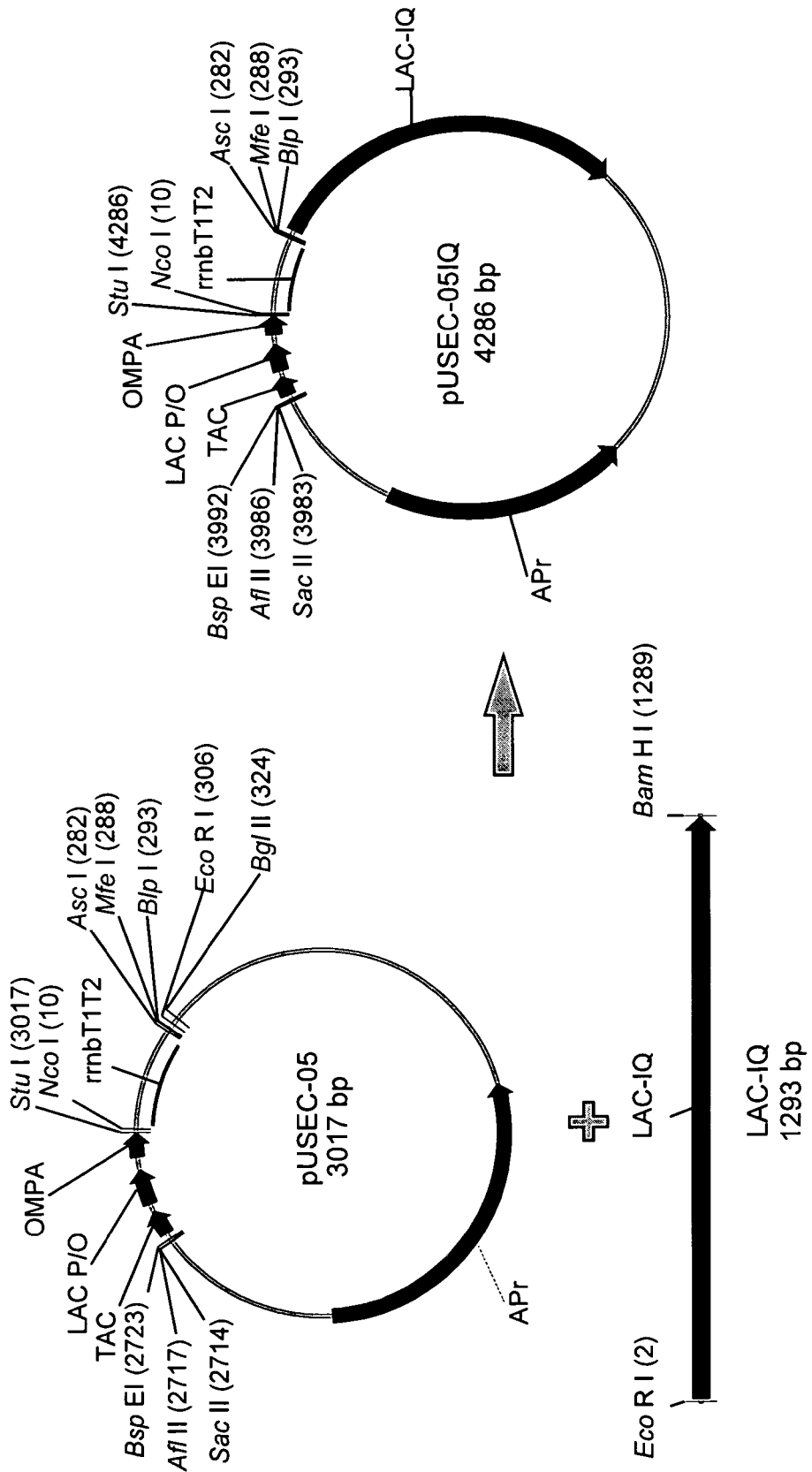

The present invention permits peptide product yields in excess of 100 mg per liter of media. It does so with novel hosts (as transformed, transfected or used in accordance with the invention), novel fermentation processes, or a combination of two or more of the foregoing.

Host Cell

The present invention provides a host cell transformed or transfected with any of the vectors of the present invention. The host cell is a genetically engineered E. coli bacterium deficient in chromosomal genes rec A and ptr encoding recombination protein A and Protease III, respectively.

Preferably, the genetically engineered E. coli bacterium is a BLR strain which already is deficient in chromosomal gene rec A. More preferably, the host cell of the present invention is a mutant BLR strain BLM6 having ATCC accession number PTA-5500.

Overview of Preferred Universal Cloning Vectors

The present invention also provides universal cloning vectors that allow for the simple construction of expression vectors such as the preferred expression vector of the present invention as indicated below.

pUSEC-05IQ Vector

One preferred universal cloning vector is the pUSEC-05IQ plasmid which is designed for the cloning of genes coding for peptides. The pUSEC-05IQ vector (FIG. 3C) contains the dual promoter block of tac and lac followed by the ompA signal sequence. Directly adjacent to the signal sequence are the unique restriction sites Stu I and Nco I that allow for the cloning of genes encoding peptides in frame with the signal sequence. Downstream of the multiple cloning site is the dual rrnB $T_1$ $T_2$ transcription terminator. The vector also carries a copy of the gene coding for the LacI$^Q$ repressor for regulation of the tac and lac promoters. The plasmid carries the ampicillin resistance gene for selection. The vector was constructed using pSP72 as the base plasmid, which carries the pUC origin of replication. The expression cassette containing the dual promoters, ompA signal, cloned peptide gene and transcription terminators can be cut from the vector with the use of three unique restriction sites located upstream and downstream of the cassette.

The utility of this vector has two components. The first utility component is in the use of this vector as a universal expression vector for the secretion of heterologous polypeptides. Using the cloning sites linked in frame with the ompA signal sequence any heterologous gene can be cloned and expressed as a secreted product. This function could be used for the rapid screening of potential gene targets without the need for cell lysis to look for expression. This utility is based on the desired function of cloning and expressing peptides that are expressed, secreted and transported via diffusion to the culture medium. The second utility component resides in the use of the six restriction sites that are used for the excision of the expression cassette. These sites are used in combination with a second vector for the cloning of multiple copies of the expression cassette for increased expression levels.

pUSEC-06 Vector

Another preferred universal cloning vector is the pUSEC-06 plasmid which acts as a secretion enhancement production vector for the cloning of up to three copies of the expression cassette cloned into pUSEC-05IQ. The pUSEC-06 vector shown in FIG. 2 contains the same six unique restriction sites flanking the expression cassette found in pUSEC-05IQ. The six sites are grouped in three pairs that can be used for individually cloning separate copies of expression cassettes. The vector contains the genes coding for the secretion factors SecE and prlA-4 (a mutant allele of SecY). The lac promoter controls the SecE gene expression and the trpA promoter controls expression of the prlA-4 gene. Tandem rrnB $T_1$ $T_2$ transcription terminators are located downstream of the SecE and prlA-4 genes. The plasmid carries a copy of the LacIQ repressor for regulation of promoters using the lac operator sequences. The kanamycin resistance gene is encoded on the vector for selection. As with pUSEC-05IQ the base vector for pUSEC-06 was pSP72 carrying the pUC origin of replication.

As with pUSEC-05IQ the utility of pUSEC-06 has two components. The pUSEC-06 vector acts as a production vehicle for increased expression of secreted proteins. The presence of the SecE and prlA-4 genes amplify the rate of secretion by increasing two of the integral components, of the Sec machinery. SecE and SecY(prlA) form the translocation domain for secretion of proteins, therefore increasing the level of these two factors increases the number of translocation domains. With an increase in translocation ability, over expressed secretion targeted proteins can be secreted across the periplasmic membrane with greater efficiency. The final result is a greater accumulation and recovery of processed peptide from the conditioned growth medium.

The second utility relates to pUSEC-05IQ. The six unique restriction sites in both pUSEC-05IQ and pUSEC-06 form the basis for the cloning of multiple expression cassettes. With the methodology described in the attached schematic up to three copies of the secretion expression cassette can be cloned creating mono, di and trigenic expression clones. The schematic represents the complete cloning of a peptide through the creation of a digenic expression vector. This novel method of increasing gene dosage on a vector could be applied to other expression systems as well.

A list of all gene components for pUSEC-05IQ and pUSEC-06 are given in Table 1.

Overview of a Preferred Expression Vector

The present invention further provides an expression vector which comprises a coding region and a control region that can easily be constructed using the above preferred universal cloning vectors (FIGS. 3A-3C). The coding region comprises nucleic acids for a peptide product of interest coupled in reading frame downstream from nucleic acids coding for a signal peptide. The control region is linked operably to the coding region and comprises a plurality of promoters and at least one ribosome binding site, wherein at least one of the promoters is selected from the group consisting of tac and lac.

Preferably, the vector comprises a plurality of transcription cassettes placed in tandem, each cassette having the control region and the coding region of the present invention. Such a digenic vector or multigenic vector is believed to provide better expression than would a dicistronic or multicistronic expression vector. This is a surprising improvement over dicistronic or multicistronic expression which is not believed to be suggested by the prior art.

The vector can optionally further comprise nucleic acids coding for a repressor peptide which represses operators associated with one or more of the promoters in the control region, a transcription terminator region, a selectable marker region and/or a region encoding at least one secretion enhancing peptide. Alternatively, in some embodiments, nucleic acids coding for a repressor peptide and a secretion enhancing peptide may be present on a separate vector co-expressed in the same host cell as the vector expressing the peptide product.

Specific examples of constructed expression vectors, and methods for constructing such expression vectors are set forth intra. Many commercially available vectors may be utilized as starting vectors for the preferred vectors of the invention. Some of the preferred regions of the vectors of the invention may already be included in the starting vector such that the number of modifications required to obtain the vector of the invention is relatively modest. Preferred starting vectors include but are not limited to pSP72 and pKK233-2. However, most preferred starting vectors are the cloning vectors of the present invention which include pUSEC-05IQ and pUSEC-06 universal direct expression cloning vectors as describes hereinbelow.

It is believed that the novel vectors of the invention impart advantages which are inherent to the vectors, and that those

TABLE 1 gene components for pUSEC-05IQ and pUSEC-06

| Vector Components | Component type | Origin or template |
| --- | --- | --- |
| Tac promoter | DNA block | Pharmacia Biosciences |
| Kanamycin resistance gene | Gene block | Pharmacia Biosciences |
| Ampicillin resistance gene | Plasmid encoded | PSP72 |
| RRNB T1-T2 | PCR fragment | Ribosomal protein gene T1 and T2 transcription terminators from pKK 233-2 |
| Lac repressor (Lac$^{IQ}$) | PCR amplified gene | pGEX 1-N plasmid |
| Lac promoter/operator | PCR amplified fragment | PGEM11ZF+ |
| ompA signal sequence | PCR amplified product | pIN IIIA |
| SEC E | PCR amplified gene | E. coli WA 837 genomic DNA |
| PRLA-4* | PCR amplified gene | Vector pRLA41 |
| TRP P/O | Assembled synthetic oligonucleotide gene | E. coli tryptophan E promoter/ operator Sequence from literature |

*PRLA-4 gene is a mutant allele of the prlA (SecY) gene.

unexpected advantages will be present even if the vectors are utilized in host cells other than the particular hosts identified as particularly useful herein, and regardless of whether the improved fermentation process described herein is utilized.

The novel fermentation process is believed to provide increased yield because of inherent advantages imparted by the fermentation process. It is believed that these advantages are particularly apparent when the preferred host cells and/or novel vectors described herein are utilized.

Notwithstanding the foregoing, one preferred embodiment of the invention simultaneously utilizes the improved expression vectors of the invention transformed into the particularly identified host cells of the invention and expressed utilizing the preferred fermentation invention described herein. When all three of these inventions are used in combination, it is believed that a significant enhancement of yield and recovery of product can be achieved relative to the prior art.

The Control Region

The control region is operably linked to the coding region and comprises a plurality of promoters and at least one ribosome binding site, wherein at least one of the promoters is selected from the group consisting of lac and tac. It has surprisingly been found that the foregoing combination of promoters in a single control region significantly increases yield of the peptide product produced by the coding region (as described in more detail intra). It had been expected that two such promoters would largely provide redundant function, and not provide any additive or synergistic effect. Experiments conducted by applicants have surprisingly shown a synergy in using the claimed combination of promoters. Other promoters are known in the art, and may be used in combination with a tac or lac promoter in accordance with the invention. Such promoters include but are not limited to lpp, ara B, trpE, gal K.

Preferably, the control region comprises exactly two promoters. When one of the promoters is tac, it is preferred that the tac promoter be 5' of another promoter in the control region. When one of the promoters is lac, the lac promoter is preferably 3' of another promoter in the control region. In one embodiment, the control region comprises both a tac promoter and a lac promoter, preferably with the lac promoter being 3' of the tac promoter.

The Coding Region

The coding region comprises nucleic acids coding for a peptide product of interest coupled in reading frame downstream from nucleic acids coding for a signal peptide whereby the coding region encodes a peptide comprising, respectively, from N terminus to C terminus the signal and the peptide product. Without intending to be bound by theory, it is believed that the signal may provide some protection to the peptide product from proteolytic degradation in addition to participating in its secretion to the periplasm.

Many peptide signal sequences are known and may be used in accordance with the invention. These include signal sequences of outer membrane proteins of well-characterized host cells, and any sequences capable of translocating the peptide product to the periplasm and of being post-translationally cleaved by the host as a result of the translocation. Useful signal peptides include but are not limited to Omp A, pel B, Omp C, Omp F, Omp T, β-la, Pho A, Pho S and Staph A.

The peptide product is preferably small enough so that, absent the present invention, it would usually require a fusion partner using prior art technology. Typically, the peptide product has a molecular weight of less than 10 KDa. More preferably, the peptide product has a C-terminal glycine, and is used as a precursor to an enzymatic amidation reaction converting the C-terminal glycine to an amino group, thus resulting in an amidated peptide. Such a conversion is described in more detail infra. Numerous biologically important peptide hormones and neurotransmitters are amidated peptides of this type. For example, the peptide product coded by the coding region may be salmon calcitonin precursor or calcitonin gene related peptide precursor, both of which have C-terminal glycines and both of which may be enzymatically amidated to mature salmon calcitonin or mature calcitonin gene related peptide. Other amidated peptides that may be produced in accordance with the invention include but are not limited to growth hormone releasing factor, vasoactive intestinal peptide and galanin. Other amidated peptides are well known in the art.

Analogs of parathyroid hormone could also be produced in accordance with the invention. For example, a peptide having the first 34 amino acids of parathyroid hormone can provide a function similar to that of parathyroid hormone itself, as may an amidated version of the 34 amino acid analog. The latter may be produced by expressing, in accordance with one or more of the expression systems and methods described herein, the first 34 amino acids of parathyroid hormone, followed by glycine-35. Enzymatic amidation as disclosed herein could then convert the glycine to an amino group. Other analogs of parathyroid hormone are also preferred, such as human parathyroid hormone analogs PTH 1-30 and PTH 1-31, in either amidated or non-amidated form.

While preferred embodiments of the direct expression system described herein produce peptides having C-terminal glycine, it is believed that any peptide will enjoy good yield and easy recovery utilizing the vectors, hosts and/or fermentation techniques described herein.

Other Optional Aspects of a Preferred Vector of The Invention or of Other Vectors to be Expressed in the Same Host as the Vector of the Invention Repressor Optionally, the preferred vector of the present invention may contain nucleic acids coding for a repressor peptide capable of repressing expression controlled by at least one of the promoters. Alternatively, however, the nucleic acids coding for a repressor peptide may be present on a separate vector in a host cell with the vector of the present invention. Appropriate repressors are known in the art for a large number of operators. Preferably, the nucleic acids coding for the repressor encode a lac repressor in preferred embodiments of the invention because it represses the lac operator that is included with both tac and lac promoters, at least one of which promoters is always present in preferred vectors of the invention.

Selectable Marker

It is preferred that any of a large number of selectable marker genes (e.g. a gene encoding kanamycin resistance) be present in the vector of the present invention. This will permit appropriate specific selection of host cells that are effectively transformed or transfected with the novel vector of the invention.

Secretion Enhancing Peptide

Nucleic acids coding for at least one secretion enhancing peptide are optionally present in the vector of the present invention. Alternatively, the nucleic acids coding for a secretion enhancing peptide may be present on a separate vector expressed in the same host cell as the vector encoding the peptide product. Preferably, the secretion enhancing peptide is selected from the group consisting of SecY (prlA) or prlA-4. It is pointed out that SecY and prlA are identical, the two terms being used as synonyms in the art. prlA-4 is a known modification of prlA and has a similar function. Another preferred secretion enhancing peptide is SecE also known as "prlG", a term used as a synonym for "SecE". Most preferably, a plurality of secretion enhancing peptides are encoded, at least one of which is SecE and the other of which is selected from the group consisting of SecY (prlA) and prlA-4. The two are believed to interact to aid translocation of the peptide product from cytoplasm to periplasm. Without intending to be bound by theory, these secretion enhancing peptides may help protect the peptide product from cytoplasmic proteases in addition to their secretion enhancing functions.

Method of Producing a Heterologous Peptide

Novel fermentation conditions are provided for growing host cells to very high cell densities under culture conditions which permit the diffusion or excretion of the peptide product into the culture medium in high yield.

Host cells useful in the novel fermentation include but are not limited to the host cells discussed supra, and/or host cells transformed or transfected with one or more of the novel expression vectors discussed supra. Other host cells genetically engineered to express peptide product together with a signal region may be used. The cells are placed in a fermenter which preferably includes appropriate means of feeding air or other gases, carbon source, and other components to the media and means for induction of the promoter. Appropriate means for monitoring oxygen content, cell density, pH and the like are also preferred.

Applicants have found that significantly improved yield of peptide product directly expressed into the culture medium is obtained by carefully controlling the average cell growth rate within a critical range between 0.05 and 0.20 doublings per hour. It is preferred that this controlled growth begin in early lag phase of the culture. It is more preferable to maintain average cell growth rate during the fermentation period (i.e. the period during which growth is being controlled as set forth herein), between 0.10 and 0.15 doublings per hour, most preferably 0.13 doublings per hour. Growth rate may be controlled by adjusting any of the parameters set forth infra in the section entitled "Production of sCTgly (Fermentation)", specifically the formula equating the feed rate "Q" to numerous other parameters. Applicants have found that varying the rate of carbon source being fed to the fermenting cells is an advantageous method of maintaining the growth rate within the critical range. In order to maintain the growth rate relatively constant, the amount of carbon source feeding into the fermenter tends to increase proportionally to the growth in number of cells.

Applicants have also discovered that significantly improved yield can be obtained by providing inducer and vitamins during said fermentation period of controlled growth. Like carbon source, feeding proper amounts of inducer involves increasing the rate of feed proportional to growth in number of cells. Since both carbon source and inducer feed preferably increase in a manner which is linked to cell growth, applicants have found that it is advantageous to mix feed and inducer together and to feed the mixture of the two at the appropriate rate for controlling cell growth (with the carbon source), thus simultaneously maintaining a continuous feed of inducer which stays at a constant ratio relative to the amount of carbon source. However, it is of course possible to feed carbon source and inducer separately. Even then, however, if a chemical inducer that may be toxic to the cells in large amounts is used, it is desirable that the inducer and carbon source be added during each hour of culturing in amounts such that the weight ratio of the inducer added in any given hour to the carbon source added in that same hour does not vary by more than 50% from the ratio of the amount of inducer added during the entirety of the fermentation process (controlled growth period) to amount of carbon source added during the entirety of the fermentation process. The 50% variance is measured from the lower ratio of two ratios being compared. For example, where the ratio of carbon source to inducer for the entire fermentation is 2 to 1, the ratio in any given hour is preferably no higher than 3 to 1 and no lower than 1.333 to 1. It is also possible to induce one or more of the promoters during growth by other means such as a shift in temperature of the culture or changing the concentration of a particular compound or nutrient.

When external carbon source feed is used as the method of controlling cell growth, it is useful to wait until any carbon sources initially in the media (prior to external carbon feed) have been depleted to the point where cell growth can no longer be supported without initiating external carbon feed. This assures that the external feed has more direct control over cell growth without significant interference from initial (non-feed) carbon sources. An oxygen source is preferably fed continuously into the fermentation media with dissolved oxygen levels being measured. An upward spike in the oxygen level indicates a significant drop in cell growth which can in turn indicate depletion of the initial carbon source and signify that it is time to start the external feed.

It has been unexpectedly found that peptide product yield increases as oxygen saturation of the fermentation media increases. This is true even though lower oxygen saturation levels are sufficient to maintain cell growth. Thus, during the entire fermentation process, it is preferred that an oxygen or oxygen enriched source be fed to the fermentation media, and that at least 20% and preferably at least 50% oxygen saturation be achieved. As used herein, "oxygen saturation" means the percentage of oxygen in the fermentation medium when the medium is completely saturated with ordinary air. In other words, fermentation media saturated with air has an "oxygen saturation" of 100%. While it is difficult to maintain oxygen saturation of the fermentation medium significantly above 100%, i.e. above the oxygen content of air, this is possible, and even desirable in view of higher oxygen content providing higher yields. This may be achieved by sparging the media with gases having higher oxygen content than air.

Significant yield improvement may be achieved by maintaining oxygen saturation in the fermentation medium at no lower than 70%, especially no lower than 80%. Those levels are relatively easy to maintain.

Faster agitation can help increase oxygen saturation. Once the fermentation medium begins to thicken, it becomes more difficult to maintain oxygen saturation, and it is recommended to feed gases with higher oxygen content than air at least at this stage. Applicants have found that ordinary air can be sufficient to maintain good oxygen saturation until relatively late in the fermentation period. Applicants have supplemented the air feed with a 50% oxygen feed or a 100% oxygen feed later in the fermentation period. Preferably, the host cell is cultured for a period between 20 and 32 hours (after beginning controlled growth), more preferably between 22 and 27 hours, more preferably for about 23-26 hours and most preferably about 24 hours. The culturing period during controlled growth is divided into two stages: a carbon source gradient feed stage followed by carbon source constant feed stage of carbon source. The inducer and vitamins are always added during both stages. The gradient feed stage is carried out preferably for about 12 to 18 hours more preferably about 15 hours while the constant feed stage is carried out preferably for about 7 to 11 hours, more preferably about 9 hours.

Preferably, the host cells are incubated at a temperature between 20 and 35° C., more preferably between 28 and 34° C., more preferably between 31.5 and 32.5° C. A temperature of 32° C. has been found optimal in several fermentations conducted by applicants.

Preferably, the pH of the culturing medium is between 6.0 and 7.5, more preferably between 6.6 and 7.0, with 6.78-6.83 (e.g. 6.8) being especially preferred.

In preferred embodiments, fermentation is carried out using hosts transformed with an expression vector having a control region that includes both a tac and a lac promoter and a coding region including nucleotides coding for a signal peptide upstream of nucleotides coding for salmon calcitonin precursor. Such an expression vector preferably includes a plurality, especially two, transcription cassettes in tandem. As used herein, the term "transcription cassettes in tandem" means that a control and coding region are followed by at least one additional control region and at least one additional coding region encoding the same peptide product as the first coding region. This is to be distinguished from the dicistronic expression in which a single control region controls expression of two copies of the coding region. The definition will permit changes in the coding region that do not relate to the peptide product, for example, insertion, in the second transcription cassette, of nucleotides coding a different signal peptide than is coded in the first transcription cassette.

Numerous carbon sources are known in the art. Glycerol has been found effective. Preferred methods of induction include the addition of chemical inducers such as IPTG and/or lactose. Other methods such as temperature shift or alterations in levels of nutrient may be used. Other induction techniques appropriate to the operator or the promoter in the control region (or one of the plurality of promoters being used where more than one appears in the control region) may also be used.

It is typical that production of peptide product drops significantly at about the same time that growth of the cells in the fermentation media becomes unsustainable within the preferred growth rate discussed supra. At that point, fermentation is stopped, carbon source and inducer feed and oxygen flow are discontinued. Preferably, the culture is quickly cooled to suppress activity of proteases and thus reduce degradation of the peptide product. It is also desirable to modify pH to a level which substantially reduces proteolytic activity. When salmon calcitonin precursor is produced using preferred vectors and host cells of the invention, proteolytic activity decreases as pH is lowered. This acidification preferably proceeds simultaneously with cooling of the media. The preferred pH ranges are discussed in more detail infra. The same assay as is being used for measuring fermentation product can be used to measure degradation at different pH levels, thus establishing the pH optimum for a given peptide and its impurities.

Recovery of the Heterologous Peptide

The present invention further provides a method for recovering the peptide product which comprises separating the host cells from the culture medium and thereafter subjecting the culturing medium to at least one type of chromatography selected from the group consisting of gel filtration, ion-exchange (preferably cation exchange when the peptide is calcitonin), reverse-phase, affinity and hydrophobic interaction chromatography. In a peptide containing cysteine residues, S-sulfonation may be carried out prior to or during the purification steps in order to prevent aggregation of the peptide and thereby increase the yield of monomeric peptide. Preferably, three chromatography steps are used in the following order: ion exchange chromatography, reverse-phase chromatography and another ion exchange chromatography.

After fermentation is completed, the pH of the culture medium is optionally altered to reduce the proteolytic activity. The assay used to measure product production can also be used to measure product degradation and to determine the best pH for stability. Where salmon calcitonin precursor is produced in accordance with the invention, a pH between 2.5 and 4.0 is preferred, especially between 3.0 and 3.5. These pH ranges also are believed to aid retention of salmon calcitonin precursor on cation exchange columns, thus providing better purification during a preferred purification technique described herein.

Also optionally, the temperature of the medium, after fermentation is completed, is lowered to a temperature below 10° C., preferably between 3° C. to 5° C., most preferably 4° C. This is also believed to reduce undesirable protease activity.

The present invention further provides a method of producing an amidated peptide product comprising the steps of: culturing, in a culture medium, any of the host cells of the present invention which express a peptide product having a C-terminal glycine; recovering said peptide product from said culture medium; amidating said peptide product by contacting said peptide product with oxygen and a reducing agent in the presence of peptidyl glycine α-amidating monooxygenase, or peptidyl glycine α-hydroxylating monooxygenase. If peptidyl glycine α-amidating monooxygenase is not used hereinabove, and if the reaction mixture is not already basic, then increasing pH of the reaction mixture until it is basic. Amidated peptide may thereafter be recovered from the reaction mixture.

EXAMPLE 1

Identification of Target Genes Responsible for Extracellular Peptide Product Degradation in Host Cells Summary Applicants identified as described below an *E. coli* metalloprotease that is responsible for degradation of extracellular sCTgly at a rate of up to 25% per hr during the 18-26 hr post induction phase of the sCTgly direct expression fermentation protocol. Degradation of sCTgly is also present prior to 17 hr at an undetermined rate. Experiments detailed below indicated that the protease responsible for the degradation of sCTgly is protease III from the ptr gene of *E. coli*.

Introduction

Protease III is 107 kDa zinc metalloprotease that preferentially degrades peptides <12 kDa. The literature indicates that the activity of Protease III resembles properties of chymotrypsin. Protease III cleaves the B chain of insulin between Tyr-Leu and between Phe-Tyr at a reduced rate. There does not appear to be a critical physiological role for Protease III and its deletion does not cause deleterious effects to the growth of the host (Dykstra et al. J. Bacteriol. 163:1055-1059; 1985). Activity of protease III has frequently been found in the growth medium especially during periods of increased secretion (Diaz-Torres et al. Can. J. Microbiol. 37: 718-721; 1991). This study summarizes experiments examining the loss of our model peptide, sCTgly, due to proteolytic activity in the culture medium during fermentations, and the mutagenesis of an *E. coli* strain for elimination of Protease III activity.

Proteolytic Degradation and Identification

Degradation of sCTgly in Conditioned Medium

Conditioned medium samples from both UGL165 (*E. coli* BLR transformed with pSCT 029) and UGL703 (*E. coli* BLR transformed with pSCT 038) Direct Expression fermentations were tested for loss of sCTgly following removal of cells and incubation of the medium spiked with sCTgly at 30° C. The concentration of sCTgly in conditioned fermentation medium was measured by CEX HPLC. Table 2 shows the data for a typical test of sCTgly degradation from a 26 hr medium sample harvested from a fermentation of UGL703. Various protease inhibitors, including Bestatin, PMSF, $\alpha_2$-macroglobulin and EDTA were tested for the ability to reduce or eliminate proteolytic degradation of sCTgly. Only EDTA was able to reduce the proteolytic degradation of sCTgly. EDTA inactivates metalloproteases by binding the divalent cations required for activity. Although EDTA was able to reduce proteolytic degradation of sCTgly, there was some residual sCTgly degradation that may be the result of other less active proteases or by residual protease III activity.

TABLE 2

Inhibition of Proteolytic Degradation by EDTA

| | Control Fermentation Medium Sample | | | 50 mM EDTA Treated Medium Sample | | |
|---|---|---|---|---|---|---|
| Incubation Time at 30° C. | sCTgly (mg/L) | % Intact | % loss from prev hr | sCTgly (mg/L) | % Intact | % loss from prev hr |
| t = 0 minutes | 241 | 100% | 0.0% | 214 | 100% | 0.0% |
| t = 60 minutes | 181 | 75% | 25% | 184 | 86% | 14% |
| t = 120 minutes | 140 | 58% | 23.6% | 179 | 84% | 2.7% |
| t = 180 minutes | 107 | 44% | 23.6% | 168 | 79% | 5.9% |

The rate of sCTgly degradation was also examined at ~18 hr post induction from a 1.25 L fermentation. Recombinant sCTgly was spiked into the 18 hr post induction harvested medium to raise the concentration of sCTgly from 37 mg/L to ~200 mg/L and incubated for 4 hrs at 30° C., then analyzed for sCTgly as above. The results are listed in Table 3.

TABLE 3

Degradation of sCTgly During Fermentation

| Incubation time 30° C. | sCTgly concentration (mg/L) |
|---|---|
| 0.0 hr | 185 |
| 2.0 hr | 99 |
| 4.0 hr | 65 |

By the end of 4 hrs the average degradation of sCTgly per hr in the 18 hr sample tested was 21% which is similar to the degradation rates of sCTgly seen from harvested fermentation medium. This result indicates that from 18 hrs post induction the degradation of sCTgly in the fermentation medium may be constant.

Identification of the Primary Extracellular Protease

The previous experiments indicated that the protease responsible for the primary degradation of sCTgly was a metalloprotease. *E. coli* Protease III is a periplasmic/extracellular zinc metalloprotease (host (Dykstra et al. J. Bacteriol. 163:1055-1059, 1985; secretion (Diaz-Torres et al. Can. J. Microbiol. 37: 718-721, 1991). The preference for zinc compared to another divalent cation, magnesium, was tested. Fermentation medium samples were pre-incubated with 50 mM EDTA for 20 minutes, then sCTgly was spiked into the sample to a final a concentration of ~250 mg/L. MgCl$_2$ or ZnCl$_2$ was added to different samples at 15 mM and incubated at 30° C. for 4 hrs. The concentration of sCTgly was measured as above and the results are listed in Table 4.

TABLE 4

Divalent Cation Specificity

| Hrs incubation | Medium alone sCTgly (mg/L) | Medium + EDTA sCTgly (mg/L) | Medium + EDTA + MgCl$_2$ sCTgly (mg/L) | Medium + EDTA + ZnCl$_2$ sCTgly (mg/L) |
|---|---|---|---|---|
| 0.0 | 175 | 295 | 241 | 244 |
| 1.0 | 155 | 223 | 219 | 194 |
| 2.0 | 103 | 211 | 199 | 140 |
| 4.0 | 23 | 193 | 175 | 67 |

The sCTgly spiked into the untreated control medium was 87% degraded after the 4 hr incubation time. Pre-treatment of the conditioned medium with EDTA prior to addition of sCTgly resulted in a loss of 34%. The addition of MgCl$_2$ and ZnCl$_2$ resulted in peptide losses of 27% and 72%, respectively. A graph of the degradation results shows similar degradation rates for the control and ZnCl$_2$ samples, as well as similar rates for the EDTA and MgCl$_2$ treated samples. The addition of the two divalent cations for the reactivation of proteolytic activity showed that zinc was effective, whereas magnesium was not.

In addition to testing the divalent cation specificity of the protease in question, experiments were performed using *E. coli* strains KS272 and SF103. *E. coli* SF103 is a K12 strain in which the ptr gene has been disrupted (described above). KS272 is the parental strain of SF103, which carries the wild type ptr gene. Fermentation experiments were performed testing proteolytic degradation of sCTgly expressed in UGL177 (KS272+pSCT 029) and UGL178 (SF103+pSCT 029).

In the first experiment, sCTgly was spiked into 0.5 L non induced fermentations of UGL177 and 178 at feed time t=0 to a concentration of 200 mg/L. A control fermentation of each strain without spiked sCTgly was also run. Samples of conditioned medium from the four fermentations were collected at 4, 18 and 20 hr post start of feed. By the time the 18 hr samples had been taken both cultures had stopped growing and were showing signs of cell death and lysis. Due to the growth problems only the medium from the 4 hr post feed time point from both UGL177 and 178 fermentations were tested for proteolytic activity. The four collected 4 hr time point medium samples were spiked with sCTgly to 200 mg/L. The sCTgly spiked samples were split and one set was treated with EDTA to 50 mM, as a control. The 8 samples were incubated for 20 hrs at room temperature (a prolonged incubation was used due to the low cell density at 4 hr post induction). The results of the incubation are listed in Table 5. The sCTgly concentrations from four of the medium samples were elevated due to the initial sCTgly spiked into the fermentation.

TABLE 5

Proteolytic Degradation of sCTgly From *E. coli* KS272 and SF103

| Incubation Time | UGL177 | | UGL178 | |
|---|---|---|---|---|
| | sCTgly (mg/L) | % sCTgly loss | sCTgly (mg/L) | % sCTgly loss |
| 0.0 hrs | 226 | 0 | 233 | 0 |
| 20.0 hrs | 129 | 42.8 | 210 | 10.1 |
| 0.0 hrs + EDTA | 204 | 0 | 198 | 0 |
| 20.0 hrs + EDTA | 161 | 20.9 | 173 | 12.4 |
| 0.0 hrs* | 323 | 0 | 346 | 0 |
| 20.0 hrs* | 212 | 34.3 | 316 | 8.7 |
| 0.0 hrs + EDTA* | 268 | 0 | 281 | 0 |
| 20.0 hrs + EDTA* | 219 | 18 | 246 | 12.3 |

*Fermentation medium samples spiked with sCTgly

The data show a difference in amount of sCTgly degradation in conditioned medium from the protease III minus strain compared to the parental strain. The parental strain exhibited almost four times the loss of sCTgly in conditioned medium samples as compared to the protease III minus strain. The degradation of sCTgly in the parental strain was approximately two fold more than the protease III minus strain even when treated with EDTA, suggesting that degradation in EDTA treated samples may be partly due to incomplete inactivation of Protease III.

The second experiment tested the ability of each strain to sustain expression of sCTgly. The two *E. coli* strains UGL177 and 178 were grown and induced using a Direct Expression fermentation protocol similar to CBK.025. Conditioned medium samples were collected for analysis at 10, 12, 14, 16 and 17 hr post induction. The two fermentation cultures had similar rates of growth confirming that the deletion of the ptr gene did not impact culture viability. However, as in the above experiment, both cultures died between 16 and 17 hr post induction. Previous tests of *E. coli* K-12 strains in the high cell density Direct Expression fermentation protocol showed decreased culture viability during the mid stages of the fermentation protocol. The production of sCTgly for the collected time points from each culture is listed in Table 6.

TABLE 6

Expression of sCTgly in UGL177 and UGL178

| Time post induction | UGL177 sCTgly (mg/L) | UGL178 sCTgly (mg/L) |
|---|---|---|
| 10.0 hr | 0.0 | 43 |
| 12.0 hr | 0.0 | 46 |
| 14.0 hr | 0.0 | 46 |
| 16.0 hr | 0.0 | 40 |
| 17.0 hr | 0.0 | 34 |

The results listed in Table V show that only the strain with the ptr gene deleted was able to accumulate sCTgly at quantifiable levels. The above results suggest that repression or elimination of *E. coli* protease III in *E. coli* production strains should offer an advantage in the production of sCTgly.

Estimation of sCTgly Loss Due to Proteolytic Activity

By assuming a conservative loss of sCTgly of 20% per hr during a UGL703 (pSCT 038 in BLR) fermentation at 30° C., it is possible to calculate the total amount of sCTgly lost during the later stages of the fermentation. This projection was based on sCTgly production data from fermentation 2301-9004 at 17 through 26 hrs post induction. The sCTgly concentration of each consecutive hour pair was averaged. The averaged sCTgly concentration was then multiplied by 0.2 to calculate the amount of sCTgly that would be degraded assuming an average degradation rate of 20% per hour. Assuming that the amount of sCTgly lost during each hr is cumulative, the amount of sCTgly lost per hr and over the course of the nine hr period could be extrapolated. The results of this extrapolation are listed in Table 7.

TABLE 7

Estimated Loss of sCTgly During Fermentation

| Time post induction | sCTgly (mg/L) | Averaged hr time points | Average sCTgly (mg/L) | 20% degradation level sCTgly (mg/L) |
|---|---|---|---|---|
| 17.0 hr | 21.6 | 17-18 hr | 22.4 | 4.5 |
| 18.0 hr | 23.2 | 18-19 hr | 24.1 | 4.8 |
| 19.0 hr | 25 | 19-20 hr | 42.25 | 8.5 |
| 20.0 hr | 59.5 | 20-21 hr | 70.15 | 14.0 |
| 21.0 hr | 90.8 | 21-22 hr | 95.15 | 19.3 |
| 22.0 hr | 99.5 | 22-23 hr | 110.0 | 22.0 |
| 23.0 hr | 120.5 | 23-24 hr | 139.9 | 28.0 |
| 24.0 hr | 159.3 | 24-25 hr | 172.2 | 34.4 |
| 25.0 hr | 185.1 | 25-26 hr | 186.6 | 37.3 |
| 26.0 hr | 188.1 | | Total sCTgly loss | 172.5 mg/L |

The level of degradation was estimated from the conditioned medium alone; degradation occurring within the cell cannot be calculated and is not included. The results shown in Table 7 suggest a loss of sCTgly of up to 171.5 mg/L over the course of the fermentation. The total sCTgly that would have been produced if the 20% degradation had not occurred can be estimated at 360 mg/l, approximately 91% higher than current production capability using the cell line UGL703.

EXAMPLE 2

Construction of a Protease Deficient *E. coli*

Disruption of ptr and recA Function in *E. coli* BL21

*E. coli* BL21 was modified by introducing disruptions in the coding regions of the ptr gene, encoding Protease III, and the recA gene. Using P1 transduction, DNA from *E. coli* SF 103 was packaged in P1 bacteria phage and used to infect *E. coli* BL21 cells. The phage cell mixture was plated on LB agar plates containing chloramphenicol; only cells containing the chloramphenicol disrupted ptr gene should have the ability to grow in the presence of chloramphenicol. Ten chloramphenicol resistant transductants were also verified for BL21 genetic markers, such as the ability to grow on lactose and streptomycin sensitivity. The resulting strains BL21Δptr were further modified by P1 transduction with the *E. coli* strain BLR, which carries a recA$^-$ genotype. The tetracycline disrupted recA$^-$ gene from BLR was used for transduction of BL21Δptr creating a BL21 ptr$^-$ recA$^-$ strain. Twenty BL21 ptr– recA– transductants were identified. The twenty isolates were given the designations BLM1-20.

Expression Analysis Using *E. coli* BLM Strains

Eight *E. coli* BLM strains BLM1-8 were transformed with the sCTgly expression vector pSCT-038 and given the designation of UGL801. Two isolates from each transformation were screened for expression of sCTgly in shake flasks. 25 mL of CPM Inoculation Medium I containing 50 ug/mL kanamycin was inoculated with 700 μL from an overnight culture of each clone. The cultures were grown to an OD 600 nm of 2-3, then induced with 150 μM IPTG and grown an additional 4 hrs. The results for the 4 hr samples and a UGL703 control are listed in Table 8. Six of the UGL801 clones were also screened in a 1.25 liter fermentation using the Direct Expression protocol outlined in CBK.025. The results from selected samples from each fermentation are listed in Table 9.

Twelve of the clones produced detectable levels of sCTgly in conditioned medium from shake flask experiments. The level of sCTgly from the twelve clones increased from 3 hr to 4 hr post induction. In contrast the UGL703 control did not show an increase from 3 hr to 4 hr post induction. The growth of the twelve clones were similar, with the exception of the two UGL801-6 clones, which reached significantly lower cell densities.

TABLE 8

Shake Flask Expression Results for UGL801 Clones

| UGL801 Clone Tested | OD 600 nm 4 hr post induction | sCTgly μg/mL 3 hr post induction | sCTgly μg/mL 4 hr post induction |
|---|---|---|---|
| UGL801-1a | 13.9 | 35 | 48 |
| UGL801-1b | 15.9 | 36 | 48 |
| UGL801-2a | 15.76 | 32 | 52 |
| UGL801-2b | 14.01 | 31 | 50 |
| UGL801-3a | 16.5 | 5.8 | 13 |
| UGL801-3b | 12.5 | 8.3 | 19 |
| UGL801-4a | 12.3 | 39 | 56 |
| UGL801-4b | 11.4 | 30 | 51 |
| UGL801-5a | 17 | 27 | 48 |
| UGL801-5b | 18.3 | 21 | 39 |
| UGL801-6a | 8.65 | 27 | 31 |
| UGL801-6b | 8.66 | 20 | 31 |
| UGL801-7a | 15.3 | 24 | 41 |
| UGL801-7b | 17.1 | 19 | 33 |
| UGL801-8a | 19.8 | 12 | 18 |
| UGL801-8b | 19.5 | 12 | 26 |
| UGL703 control | 15.7 | 33 | 35 |

Six clones (UGL801-1a, 2a, 3a, 4a, 5a, and 6a) were tested for expression of sCTgly using Direct Expression fermentation protocols, in a 1.25 L fermentation. All of the fermentations produced sCTgly at levels above 170 mg/L with most reaching maximum production of 200+ mg/L. All of the clones except UGL801-6a produced maximum levels of sCTgly prior to end of the fermentation protocol at 26 hr post induction (see Table 9). Samples from these fermentations contained large amounts of precipitation after pH adjustment to 3.0 as per standard procedures. The single exception to this phenomenon was UGL801-6a, which produced sCTgly up to 26 hr post induction and did not show precipitation in medium samples adjusted to pH 3.0. UGL801-6a also produced the highest expression level of sCTgly reaching 256 mg/L in conditioned medium at 26 hr post induction. UGL801-6a also had the highest wet cell weight of all the runs listed in Table 9. Based on data obtained from the test fermentations, UGL801-6a was chosen for further development of sCTgly production. The corresponding host strain BLM-6 (ATCC Accession Number PTA-5500) was used as the preferred cell line for insertion of other peptide-gene containing plasmids.

TABLE 9

Productivity Results For UGL801 Fermentations

| UGL801 Clone | Reference | Max wet cell weight g/L/hrs post induction | Max sCTgly production mg/L/hrs post induction |
|---|---|---|---|
| UGL801-1a | CPM:15:185 | 116/26 hr | 212/25 hr |
| UGL801-2a | CPM:15:190 | 111/26 hr | 183/25 hr |
| UGL801-3a | CPM:15:210 | 117/25 hr | 211/23 hr |
| UGL801-4a | CPM:15:200 | 105/25 hr | 226/23 hr |
| UGL801-5a | CPM:15:205 | 114/25 hr | 180/24 hr |
| UGL801-6a | CPM:15:195 | 153/26 hr | 256/26 hr |

UGL801-6a is now designated as UGL801 (ATCC Accession Number PTA-5501) and is chosen for further development and scale up for production. The *E. coli* host strain BLM-6 (F$^-$ ompT hsdS$_B$ (r$_B^-$m$_B^-$) gal dcm Δ(srl-recA)306::Tn10(Tc$^R$) ptr32::ΩCat$^R$) (ATCC Accession Number PTA-5500), which is the host for UGL801 is be used as the preferred host for expression cell lines. Accordingly, BLM-6 was used for insertion of expression vectors expressing PTH 1-31 gly and PTH 1-34gly generating cell lines UGL810 (ATCC Accession Number PTA-5502) and UGL820 (ATCC Accession Number PTA 5569), respectively.

EXAMPLE 3

Fermentation Protocol for UGL801

As indicated above, the plasmid vector, pSCT038, was used to transform the BLM-6 host strain to yield the UGL801 recombinant cell line. The development of optimized fermentation conditions for the new cell line, UGL801, began with the evaluation of the UGL801 cell line to produce sCTgly using the UGL703 Direct Expression conditions (the cell line, UGL703, is *E. coli* BLR harboring the plasmid pSCT038): substrate limited fed batch fermentation run at 30° C., pH6.6, dO$_2 \geq$70%, 26 hours of induced feed in a medium developed for UGL703. UGL703 in the initial DE fermentation protocol resulted in a volumetric yield of <200 mg/L and a specific yield of ~1.3 mg of extracellular sCTgly per gram wet cell weight of cells. Host cell modifications resulted in the host cell, BLM-6, and the recombinant cell line, UGL801, which when tested under the UGL703 fermentation conditions showed ~1.3× volumetric increase to greater than 200 mg/L at 26 hours post induction and a 1.2× increase in specific yield at 26 hours post induction. These data are shown in Table 10. The introduction of the UGL801 cell line with its reduced protease background and it's ability to grow and produce un-degraded recombinant protein earlier in the fermentation were significant improvements in yield and process reliability.

TABLE 10

A comparison of Specific Productivity and Volumetric Productivity of UGL703 and UGL801 with no changes in the fermentation conditions.

| Hrs post feed | Specific Productivity | | | Volumetric Productivity | | |
|---|---|---|---|---|---|---|
| | UGL703 DE Fermentation Conditions | UGL801 w/UGL703 Conditions | Fold Increase | UGL703 DE Fermentation Conditions | UGL801 w/UGL703 Conditions | Fold Increase |
| 19 | 0.4 | 1.9 | 5.2 | 32 | 164 | 5.1 |
| 20 | 0.6 | | | 55 | | |
| 21 | 0.6 | 1.8 | 3.2 | 59 | 182 | 3.1 |
| 22 | 1.0 | | | 108 | | |
| 23 | 0.9 | 1.8 | 2.0 | 108 | 207 | 1.9 |
| 24 | 1.3 | 1.7 | 1.3 | 160 | 217 | 1.4 |
| 25 | 1.3 | 1.7 | 1.3 | 177 | 221 | 1.2 |
| 26 | 1.3 | 1.6 | 1.2 | 184 | 230 | 1.3 |

After directly comparing the results of the two cell lines in the same fermentation protocol, a series of optimization studies of the fermentation parameters was performed, including: increased temperature; changes in Feed/induction program; addition of new media components; and extension of the Feed/induction period.

Increased Temperature

During the development of the new host cell, BLM-6, an investigation into the characteristics of the protease degradation at the temperature of fermentation had shown that there was rapid degradation of the glycine-extended peptide at >30° C. when using the predecessor host cell BLR. The new protease deficit strain, BLM-6, had a reduced extracellular protease array, suggesting that it could be grown at a higher temperature to produce potentially more mass and more product. While maintaining the fermentation pH at 6.6, the temperature of the entire fermentation, both batch and fed-batch stages, was increased to 32° C. The new BLM-6 based recombinant cell line, UGL801, grew well at the increased temperature and expressed the sCTgly. As seen in Table 11, the volumetric and specific productivities of the new cell line with the increased temperature of fermentation were increased.

TABLE 11

The comparison of productivity values of the UGL801 fermentation with increased temperature (32° C.) to the initial UGL801 fermentation done according to the UGL703 DE fermentation conditions. The fold increase of the specific productivity with the temperature increase is also shown

| Hrs Post Feed | UGL801 with UGL703 Fermentation Conditions | | UGL801 with Increased Temperature of Fermentation | | |
|---|---|---|---|---|---|
| | Volumetric Productivity, mg/L | Specific Productivity, mg/gram | Volumetric Productivity, mg/L | Specific Productivity, mg/gram | Fold Increase |
| 19 | 164 | 1.9 | 239 | 3.0 | 1.5 |
| 21 | 182 | 1.8 | 283 | 3.3 | 1.8 |
| 23 | 207 | 1.8 | 312 | 3.4 | 1.9 |
| 24 | 217 | 1.7 | 298 | 3.0 | 1.7 |
| 25 | 221 | 1.7 | 276 | 2.7 | 1.6 |
| 26 | 230 | 1.6 | 286 | 2.2 | 1.4 |

Figure 2A:
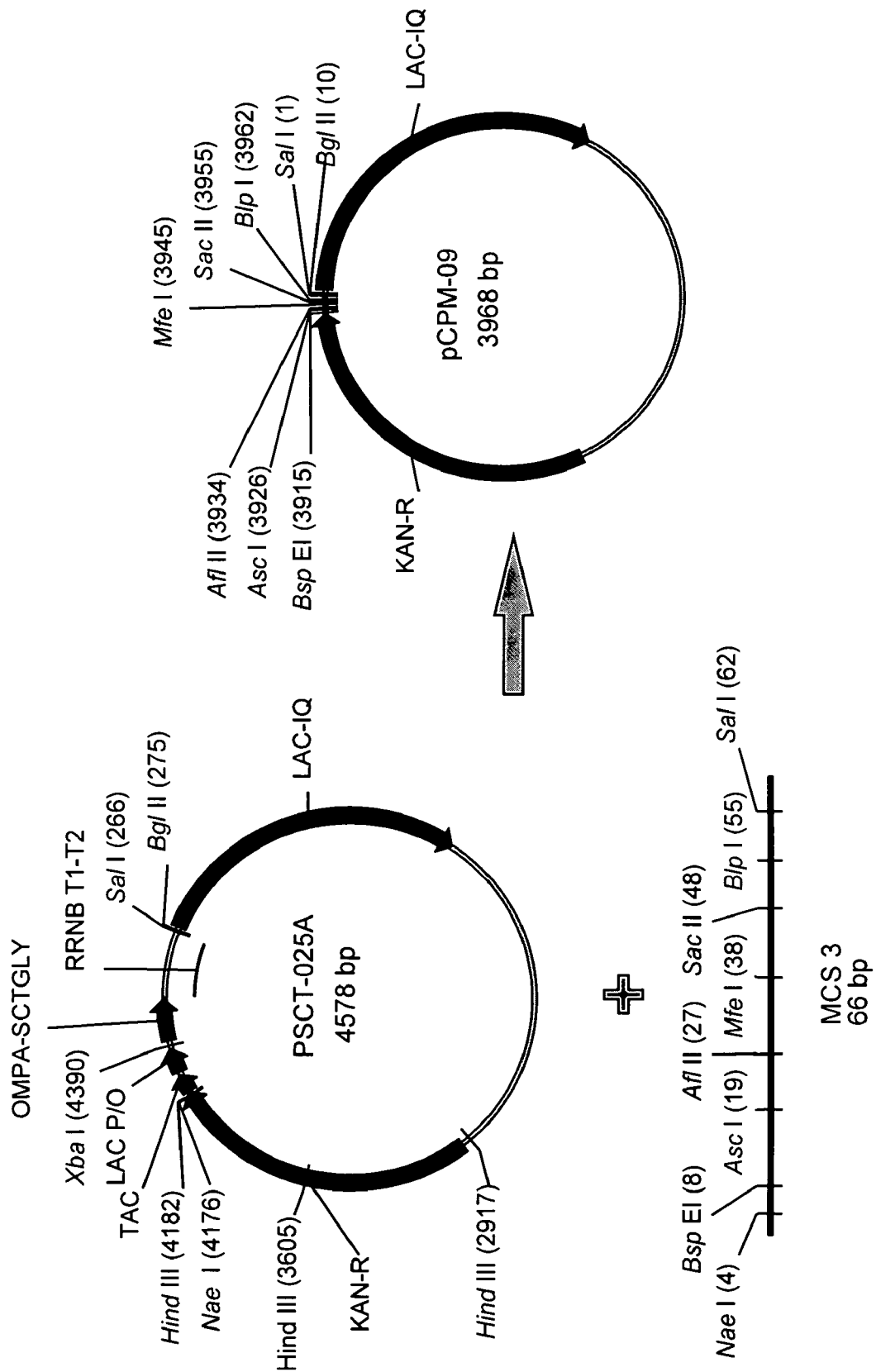
FIGS. 2A and 2B show a schematic diagram of the construction of the pCPM-00 vector (2A) which is used in the construction of the pUSEC-06 vector (2B)(ATCC Accession Number PTA-5568).
Figure 2B:
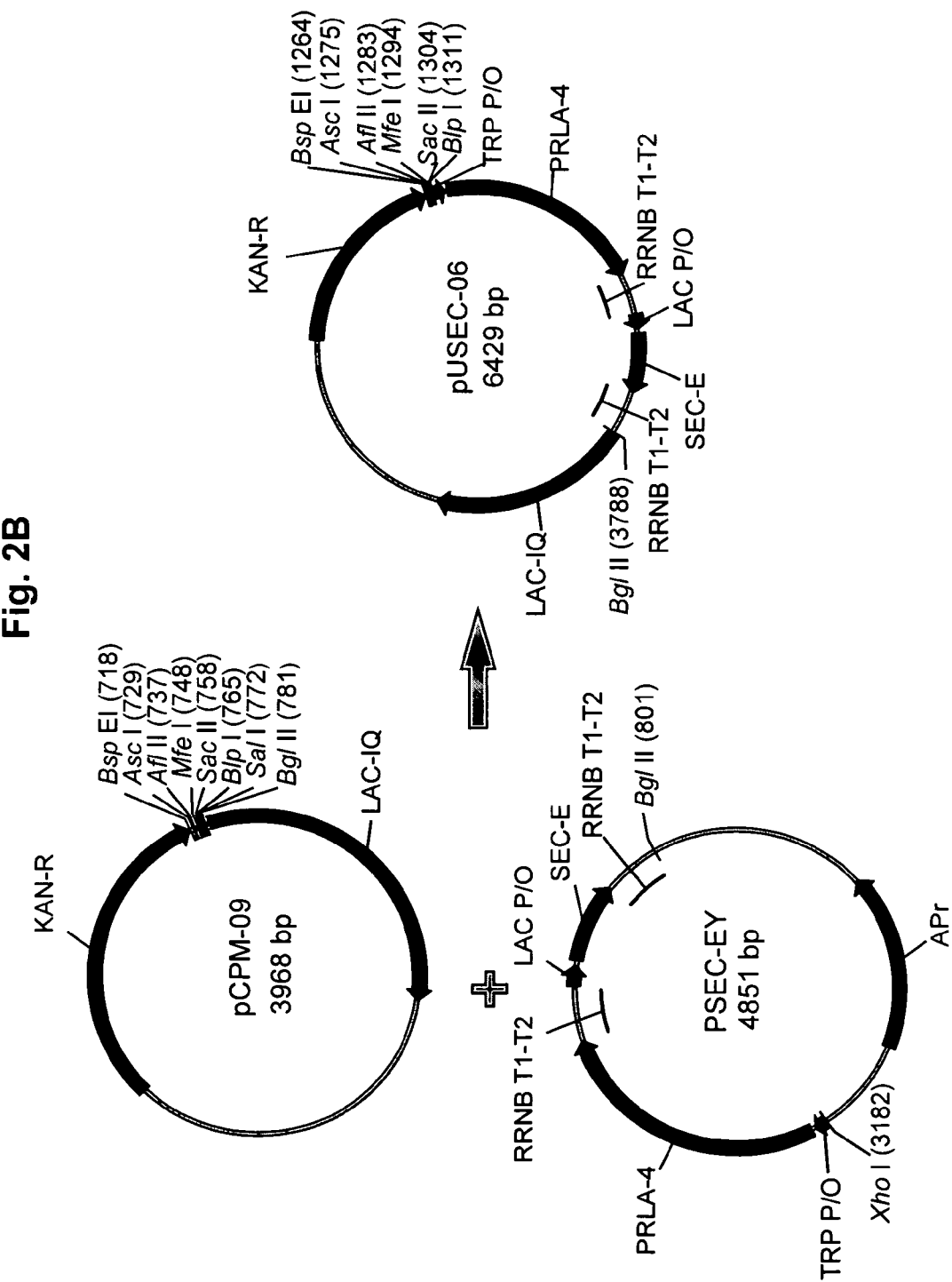
Figure 4:
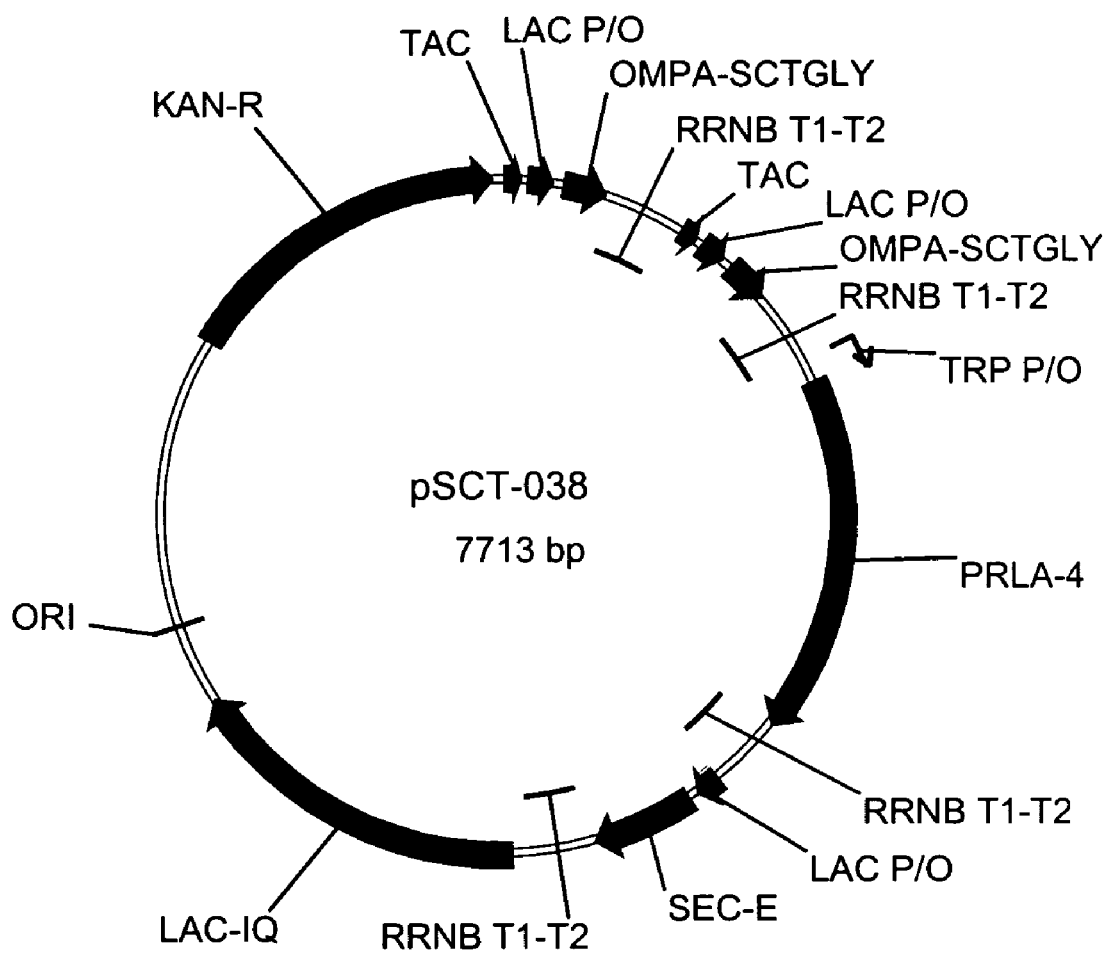
FIG. 4 shows a schematic diagram of the construction of the pSCT-038 vector. pSCT-038 was used to transform E. coli BLR and BLM-6 and produce the digenic UGL 703 and UGL801 clones, respectively.

As can be seen in the graphs in FIG. 2, the productivity at the increased temperature was not stable for the entire fed batch (induction) period of the fermentation protocol. Further developmental investigation was indicated.

Changes in Feed/Induction Program

The exponential feed program developed for the Direct Expression fermentation procedure of UGL703 (BLR::pSCT038) was altered in an attempt to increase the per cell productivity. The rate of feed medium addition was held constant at the feed rate at the 20 hour post induction time until the end of the run at 26 hours post induction. The results of this change are shown in Table 12.

TABLE 12

Comparison of the UGL801 Productivity with the alteration in the feed program to allow for a constant feed rate between 20 and 26 hours post induction. The fold increase of the improvement is also presented

| Hrs Post Induction | UGL801, with Increased Temperature of Fermentation | | UGL801 Constant Feed Rate 20-26 hours | | Fold Increase |
|---|---|---|---|---|---|
| | Volumetric Productivity, mg/L | Specific Productivity, mg/gram | Volumetric Productivity, mg/L | Specific Productivity, mg/gram | |
| 19 | 239 | 3.0 | 255 | 3.5 | 1.2 |
| 21 | 283 | 3.3 | 300 | 3.8 | 1.2 |
| 22 | | | 341 | 4.2 | |
| 23 | 312 | 3.4 | 335 | 3.9 | 1.1 |
| 24 | 298 | 3.0 | 341 | 4.0 | 1.3 |
| 25 | 276 | 2.7 | 366 | 4.0 | 1.5 |
| 26 | 286 | 2.2 | 372 | 4.0 | 1.8 |

Addition of New Media Components

It is generally assumed that most vitamins and trace elements necessary to cell growth are provided for the cell via the addition of a yeast extract. However, as the protein synthesis demands on these recombinant cells were increased, the need for additional vitamins and trace elements was recognized. The feed medium was supplemented with a vitamin/trace element mixture; the results of the fermentation experiments showed that the addition of the mixture offered a level of stabilization to the fermentation productivity. The productivity and reproducibility with the addition of the vitamin/trace element mixture suggested that the constant feed period could be extended beyond the 26 hours.

TABLE 13

Comparison of the UGL801 Productivity with the addition of a mixture of vitamins and trace elements during the entire feed/induction period of 26 hours. The fold increase of the improvement is also presented

| Hrs Post Induction | UGL801 Constant Feed Rate 20-26 hours | | UGL801, plus vitamins and trace elements | | Fold Increase |
|---|---|---|---|---|---|
| | Volumetric Productivity, mg/L | Specific Productivity, mg/gram | Volumetric Productivity, mg/L | Specific Productivity, mg/gram | |
| 19 | 255 | 3.5 | 235 | 3.2 | 0.9 |
| 21 | 300 | 3.8 | 288 | 3.4 | 0.9 |
| 22 | 341 | 4.2 | | | |
| 23 | 335 | 3.9 | 336 | 3.8 | 1.0 |
| 24 | 341 | 4.0 | 350 | 3.9 | 1.0 |
| 25 | 366 | 4.0 | 366 | 4.0 | 1.0 |
| 26 | 372 | 4.0 | 378 | 4.0 | 1.0 |

Extension of the Feed/Induction Period

The feasibility of extending the fermentation period of fed-batch and induction was evaluated. The basis for the extension was the feed rate at 20 hours when extended to 26 hours showed constant production of extracellular peptide with minimal increase in the wet cell weight. The supplementation of the feed medium with vitamins/trace elements suggested that the fermentation was sufficiently stable to extend the length of the induction period to beyond 26 hours. The fermentation feed/induction period was extended incrementally to 29 hours. Other data suggested that 29 hours might be the limit of the productive period of the fermentation without loss of protein or evidence of cell lysis. The fermentation feed/induction period was extended to 29 hours at the constant feed rate established at 20 hours.

TABLE 14

Productivities with the addition of the extended feed/induction period. The fold increase before the extension is constant, however, during the extra three hours the yield continues to increase approximately 20%

| Hrs Post Induction | UGL801 plus vitamins and trace elements | | UGL801: Final Optimized Fermentation, Constant Feed 20-29 Hours | | Fold Increase |
|---|---|---|---|---|---|
| | Volumetric Productivity, mg/L | Specific Productivity, mg/gram | Volumetric Productivity, mg/L | Specific Productivity, mg/gram | |
| 19 | 231 | 3.2 | 253 | 3.1 | 1.0 |
| 21 | 283 | 3.4 | 288 | 3.3 | 1.0 |
| 23 | 338 | 3.8 | 345 | 3.7 | 1.0 |
| 24 | 356 | 4.0 | 364 | 3.8 | 1.0 |
| 25 | 381 | 4.1 | 385 | 4.1 | 1.0 |
| 26 | 403 | 4.2 | 409 | 4.2 | 1.0 |
| 27 | | | 429 | 4.3 | |
| 28 | | | 436 | 4.3 | |
| 29 | | | 461 | 4.5 | |

The fermentation development and optimization for UGL801, *E. coli* BLM-6::pSCT038, resulted in a 2.6 fold increase in the extracellular production of sCTgly per gram (wet cell weight) of cell mass when the productivity of the cell line under UGL703 conditions was directly compared to the final optimized productivity of UGL801.

The following Table 15 lists the medium components used in different fermentations.

TABLE 15

| Components (CPM I media) | Components (UGL 703 Batch Medium) | Components (UGL801 Batch Medium) |
|---|---|---|
| $(NH_4)_2SO_4$ | $(NH_4)_2SO_4$ | $(NH_4)_2SO_4$ |
| $KH_2PO_4$ | $KH_2PO_4$ | $KH_2PO_4$ |
| $MgSO_4$—$7H_2O$ | $MgSO_4$—$7H_2O$ | $MgSO_4$—$7H_2O$ |
| $CaC_{12}$ | $CaCl_{12}$ | $CaCl_{12}$ |
| $FeSO_4$—$7H_2O$ | $FeSO_4$—$7H_2O$ | $FeSO_4$—$7H_2O$ |
| $Na_3$ Citrate | $Na_3$ Citrate | $Na_3$ Citrate |
| N-Z Case+ | N-Z Case+ | N-Z Case+ |
| Hy Yest 412 | Hy Yest 412 | Hy Yest 412 |
| L-methionine | L-methionine | L-methionine |
| Kanamycin | Kanamycin | Kanamycin |
| Glycerol | Glycerol | Glycerol |
| | Feed Medium Components | Feed Medium Components |
| | L-leucine | L-leucine |
| | Kanamycin | Kanamycin |
| | Glycine | Vitamins/Trace Elements |
| | Glycerol | Glycine |
| | | Glycerol |

CONCLUSION

UGL703 in the Direct Expression fermentation protocol produced extracellular sCTgly at volumetric levels of <200 mg/L and specific productivity of ~1.3 mg peptide per gram of wet cell weight of cells. The creation of the host cell BLM-6 offered the first improvement in productivity by reducing the background level of proteases. When BLM-6 was used as the host for the original plasmid vector, pSCT038, the result was UGL801 with a 20-30% improvement in productivity. Additional improvements described in this document were made to the fermentation protocol to optimize the volumetric and specific productivities. The following tables are summary comparisons of volumetric and specific productivities starting with UGL703 and progressing through the new cell line, UGL801, and the four improvements made to optimize the fermentation protocol. The sum of the fermentation improvements increased the volumetric productivity of UGL801 2.2 fold comparing data at 26 hours post induction, while the specific productivity at 26 hours pi increased more than 3 fold (3.2). The extension of the run to 29 hours gave ~12% volumetric increase. There was a 3.46 fold increase in the specific productivity of the final fermentation protocol for UGL801 at 29 hours post induction when compared to the specific productivity at 26 hours for UGL703.

TABLE 16

Volumetric Productivity from UGL703 to optimized UGL801

| Hrs post feed | UGL703 VP | UGL801 VP according to UGL703 | UGL801 VP w/inc temp | UGL801 VP constant feed rate @20 hrs | UGL801 VP plus vit/TE | UGL801 extended feed rate |
|---|---|---|---|---|---|---|
| 19 | 32 | 164 | 239 | 255 | 231 | 253 |
| 20 | 55 | | | | | |

TABLE 16-continued

Volumetric Productivity from UGL703 to optimized UGL801

Volumetric Productivity

| Hrs post feed | UGL703 VP | UGL801 VP according to UGL703 | UGL801 VP w/inc temp | UGL801 VP constant feed rate @20 hrs | UGL801 VP plus vit/TE | UGL801 VP extended feed rate |
|---|---|---|---|---|---|---|
| 21 | 59 | 182 | 283 | 300 | 283 | 288 |
| 22 | 108 | | | | | |
| 23 | 108 | 207 | 312 | 335 | 338 | 345 |
| 24 | 160 | 217 | 298 | 341 | 356 | 364 |
| 25 | 177 | 221 | 276 | 366 | 381 | 385 |
| 26 | 184 | 230 | 286 | 372 | 403 | 409 |
| 27 | | | | | | 429 |
| 28 | | | | | | 436 |
| 29 | | | | | | 461 |

TABLE 17

Specific Productivity from UGL703 to optimized UGL801

Specific Productivity

| Hrs post feed | UGL703 SP | UGL801 SP according to UGL703 | UGL801 SP w/ inc temp | UGL801 SP constant feed rate @ 20 hrs | UGL801 SP plus vit/TE | UGL801 SP extended feed rate |
|---|---|---|---|---|---|---|
| 19 | 0.4 | 1.9 | 3.0 | 3.5 | 3.2 | 3.1 |
| 20 | 0.6 | | | | | |
| 21 | 0.6 | 1.8 | 3.3 | 3.8 | 3.4 | 3.3 |
| 22 | 1.0 | | | 4.2 | | |
| 23 | 0.9 | 1.8 | 3.4 | 3.9 | 3.8 | 3.7 |
| 24 | 1.3 | 1.7 | 3.0 | 4 | 3.9 | 3.8 |
| 25 | 1.3 | 1.7 | 2.7 | 4 | 4.0 | 4.1 |
| 26 | 1.3 | 1.6 | 2.2 | 4 | 4.0 | 4.2 |
| 27 | | | | | | 4.3 |
| 28 | | | | | | 4.3 |
| 29 | | | | | | 4.5 |

Although the present invention has been described in relation to particular embodiments thereof, many other variations and modifications and other uses will become apparent to those skilled in the art. The present invention therefore is not limited by the specific disclosure herein, but only by the appended claims.

What is claimed is:

1. A recombinant cell line UGL820 having ATCC Accession Number PTA-5569.

* * * * *